United States Patent
Gundy et al.

(10) Patent No.: US 9,205,165 B2
(45) Date of Patent: Dec. 8, 2015

(54) VOLATILE MATERIAL DISPENSING SYSTEM HAVING AN ADJUSTABLE DIFFUSION APPARATUS

(71) Applicant: S.C. Johnson & Son, Inc., Racine, WI (US)

(72) Inventors: Jill Tyler Gundy, Lindenhurst, IL (US); Sandra D. Tschantz, Kenosha, WI (US); Mark E. Johnson, Woodstock, IL (US); Ronald M. Llanes, Lisle, IL (US); David Nebel, Chicago, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 514 days.

(21) Appl. No.: 13/657,686

(22) Filed: Oct. 22, 2012

(65) Prior Publication Data
US 2014/0110495 A1    Apr. 24, 2014

(51) Int. Cl.
*A61L 9/12* (2006.01)

(52) U.S. Cl.
CPC . *A61L 9/127* (2013.01); *A61L 9/12* (2013.01); *A61L 2209/11* (2013.01); *A61L 2209/131* (2013.01); *A61L 2209/133* (2013.01)

(58) Field of Classification Search
CPC ............. A61L 9/04; A61L 9/12; A61L 9/127; A61L 2209/10; A61L 2209/131; A61L 2209/133
See application file for complete search history.

(56) References Cited

U.S. PATENT DOCUMENTS

| | | | |
|---|---|---|---|
| 1,742,962 | A | 1/1930 | McCrosky |
| 2,180,752 | A | 11/1939 | Weiss |
| 3,727,840 | A | 4/1973 | Nigro |
| 3,964,684 | A | 6/1976 | Schimanski |
| 4,161,284 | A | 7/1979 | Rattan |
| 4,254,910 | A | 3/1981 | Martin |
| 4,257,558 | A | 3/1981 | Mason, Jr. |
| 4,339,079 | A | 7/1982 | Sato et al. |
| 4,345,716 | A | 8/1982 | Armstrong et al. |
| 4,502,630 | A | 3/1985 | Haworth et al. |
| 4,526,320 | A | 7/1985 | von Philipp et al. |
| 4,534,509 | A | 8/1985 | Holzner |
| 4,558,820 | A | 12/1985 | Harris, Jr. |
| 4,583,686 | A | 4/1986 | Martens et al. |
| 4,630,775 | A | 12/1986 | Mandon et al. |
| 4,660,763 | A * | 4/1987 | Gutkowski et al. ............. 239/43 |
| 4,762,275 | A | 8/1988 | Herbert et al. |

(Continued)

FOREIGN PATENT DOCUMENTS

| | | |
|---|---|---|
| EP | 0722743 A2 | 7/1996 |
| GB | 386298 A | 1/1933 |

(Continued)

OTHER PUBLICATIONS

PCT/US2013/065580 International Search Report and Written Opinion dated Feb. 17, 2014.

*Primary Examiner* — Ryan Reis

(57) ABSTRACT

A volatile material dispensing system includes a housing having at least one opening in a sidewall thereof and at least one engagement member extending from the housing. The volatile material dispensing system further includes a base adapted to interact with the housing, wherein the base includes a mechanical assembly. A reservoir contains a volatile material, wherein the reservoir rotates from a first position to a second position when the at least one engagement member contacts the mechanical assembly.

17 Claims, 18 Drawing Sheets

(56) References Cited

U.S. PATENT DOCUMENTS

| | | | |
|---|---|---|---|
| 4,844,251 A | 7/1989 | Gueret | |
| 4,995,555 A | 2/1991 | Woodruff | |
| 4,998,671 A | 3/1991 | Leifheit | |
| 5,126,070 A | 6/1992 | Leifheit et al. | |
| 5,178,327 A * | 1/1993 | Palamand et al. | 239/57 |
| 5,269,460 A * | 12/1993 | Hautmann | 239/35 |
| 5,282,572 A | 2/1994 | Fuller | |
| 5,458,244 A | 10/1995 | Emori | |
| 5,788,155 A | 8/1998 | Martin et al. | |
| 5,851,442 A * | 12/1998 | Spector | 261/30 |
| 5,875,968 A | 3/1999 | Miller et al. | |
| 6,080,367 A | 6/2000 | Lin | |
| 6,162,454 A | 12/2000 | Ahr et al. | |
| 6,334,449 B1 | 1/2002 | Burrowes et al. | |
| 6,481,639 B1 * | 11/2002 | Pozzo | 239/47 |
| 6,569,387 B1 | 5/2003 | Furner et al. | |
| 6,638,588 B1 | 10/2003 | Bowen et al. | |
| 6,705,541 B2 | 3/2004 | Schuehrer et al. | |
| 6,863,960 B2 | 3/2005 | Curro et al. | |
| 6,918,710 B2 | 7/2005 | Budds et al. | |
| 6,991,842 B2 | 1/2006 | Hurwitz | |
| 7,021,848 B1 | 4/2006 | Gruenbacher et al. | |
| RE39,204 E | 7/2006 | Hurry et al. | |
| 7,100,805 B2 | 9/2006 | Bulsink | |
| 7,108,440 B1 | 9/2006 | Gruenbacher et al. | |
| 7,213,770 B2 | 5/2007 | Martens, III et al. | |
| 7,323,035 B2 | 1/2008 | Robinson et al. | |
| 7,556,191 B2 | 7/2009 | Hewitt et al. | |
| 7,715,699 B2 | 5/2010 | Lamers et al. | |
| 7,841,587 B2 | 11/2010 | Pankhurst et al. | |
| 8,062,598 B2 | 11/2011 | Bertassi et al. | |
| 8,406,616 B2 | 3/2013 | Pedrotti | |
| 2004/0003724 A1 * | 1/2004 | Ellis | 96/115 |
| 2004/0009103 A1 * | 1/2004 | Westring | 422/125 |
| 2004/0134999 A1 * | 7/2004 | Aiyama | 239/47 |
| 2006/0032937 A1 | 2/2006 | Caserta et al. | |
| 2009/0218413 A1 | 9/2009 | Withers | |
| 2009/0302128 A1 | 12/2009 | Zobele | |
| 2009/0308947 A1 | 12/2009 | Althouse et al. | |
| 2010/0264232 A1 | 10/2010 | Gruenbacher et al. | |
| 2010/0308126 A1 | 12/2010 | Gruenbacher et al. | |
| 2010/0308130 A1 | 12/2010 | Gruenbacher et al. | |
| 2010/0314461 A1 | 12/2010 | Gruenbacher et al. | |
| 2011/0132992 A1 | 6/2011 | Hoppe et al. | |
| 2011/0180621 A1 | 7/2011 | Gruenbacher et al. | |
| 2011/0194983 A1 | 8/2011 | Gough et al. | |
| 2012/0018527 A1 | 1/2012 | Duddington et al. | |
| 2012/0275932 A1 * | 11/2012 | Sharma | 417/66 |

FOREIGN PATENT DOCUMENTS

| | | |
|---|---|---|
| GB | 2349089 A | 10/2000 |
| JP | 2002-144686 A | 5/2002 |
| WO | 9712517 | 4/1997 |
| WO | 9712518 | 4/1997 |
| WO | 9742983 | 11/1997 |
| WO | 9844961 | 10/1998 |
| WO | 03000162 | 1/2003 |
| WO | 03105652 A2 | 12/2003 |
| WO | 2005021054 | 3/2005 |
| WO | 2006006279 | 1/2006 |
| WO | 2006114987 | 11/2006 |
| WO | 2007008531 | 1/2007 |
| WO | 2007030143 | 3/2007 |
| WO | 2007032096 | 3/2007 |
| WO | 2007129698 | 11/2007 |
| WO | 2008038706 | 4/2008 |
| WO | 2008072361 | 6/2008 |
| WO | 2009014153 | 1/2009 |
| WO | 2009107813 | 9/2009 |
| WO | 2009107814 | 9/2009 |
| WO | 2010070836 | 6/2010 |
| WO | 2010120960 | 10/2010 |
| WO | 2010120961 | 10/2010 |
| WO | 2010121039 | 10/2010 |
| WO | 2011040580 | 7/2011 |
| WO | 2011162201 | 12/2011 |

* cited by examiner

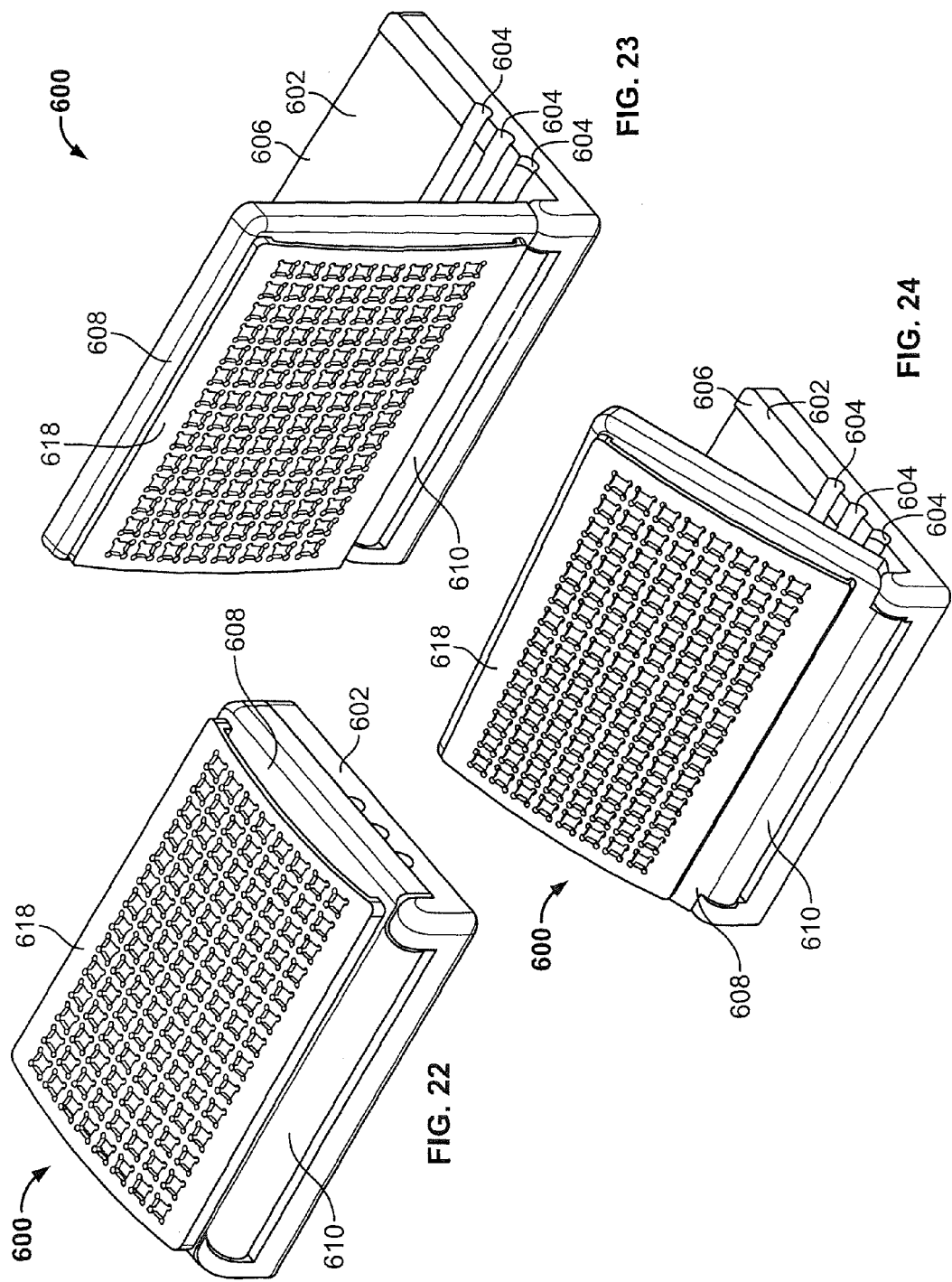

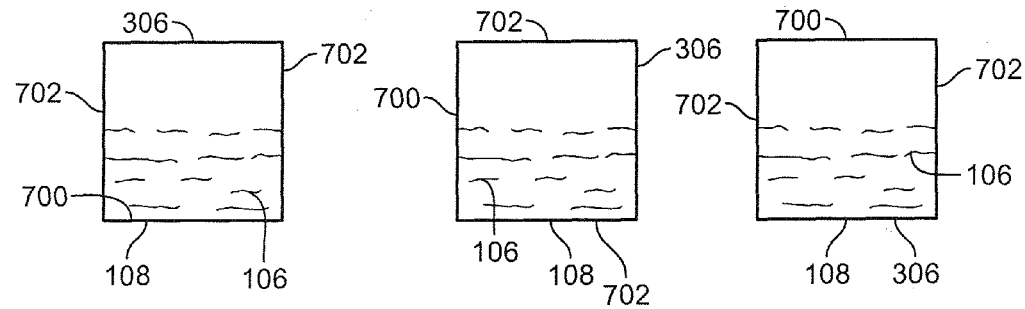
FIG. 25A    FIG. 25B    FIG. 25C
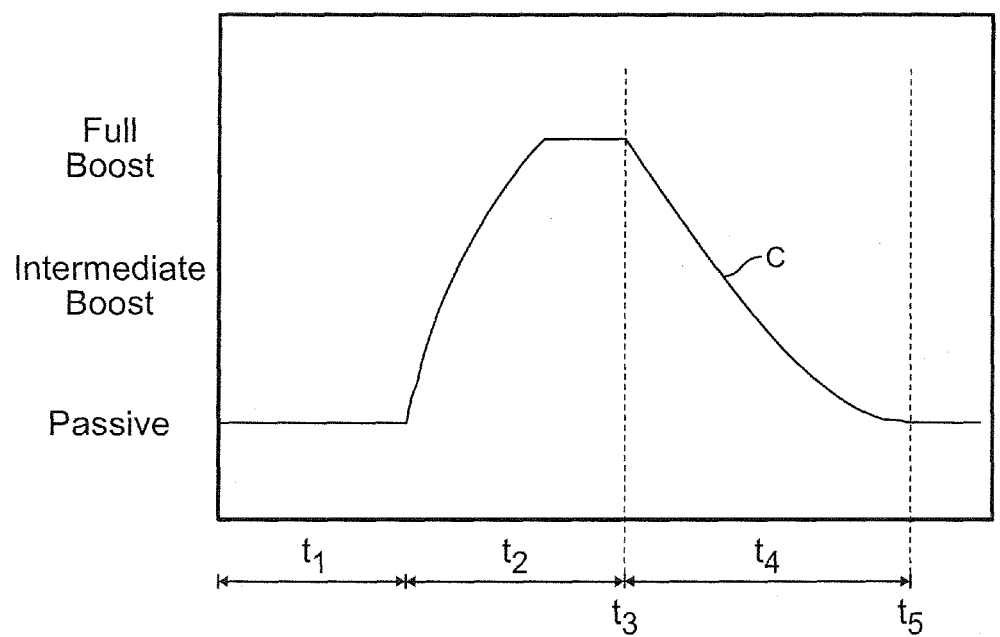
FIG. 26

VOLATILE MATERIAL DISPENSING SYSTEM HAVING AN ADJUSTABLE DIFFUSION APPARATUS

CROSS REFERENCE TO RELATED APPLICATIONS

None.

REFERENCE REGARDING FEDERALLY SPONSORED RESEARCH OR DEVELOPMENT

Not applicable.

SEQUENTIAL LISTING

Not applicable.

BACKGROUND OF THE DISCLOSURE

1. Field of the Disclosure

The present disclosure relates to a volatile material dispensing system having an adjustable diffusion apparatus adapted to regulate the emission of a volatile material, and in particular, to a volatile material dispensing system having a mechanical assembly that is configured to rotate a reservoir, whereby the rotation causes increased diffusion of the volatile material from the dispensing system in a plurality of operating conditions including a passive state, a complete boost state, and an alternative intermediate active state.

2. Description of the Background of the Disclosure

Various volatile material dispensing devices are known in the prior art that generally comprise a reservoir that holds the volatile material and optionally include a housing to retain the reservoir. The prior art volatile material dispensing devices typically either allow passive diffusion of the volatile material to occur without the aid of a dispensing mechanism or enhance and/or facilitate the release of the volatile material using a dispensing mechanism. Typical dispensing mechanisms used in volatile material dispensing devices include a heating apparatus and/or a fan that either heats and/or supplies air, respectively. However, such dispensing mechanisms may add an increased manufacturing cost to the device and an increased operating cost due to the need for electrical power.

Both passive and heat-based diffusion devices suffer from limited diffusion options. In particular, some diffusion devices are only capable of operating in a finite number of operating conditions. For example, such devices may operate only in a passive state, only in an active state, or only in a limited number of active states. Further, such operation is typically pre-programmed such that the operator of the device can only control the diffusion rate indirectly, e.g., when a fan or heater is adjusted to increase or decrease the air flow and/or heat flow over the volatile material, respectively.

In contrast, the volatile material dispensing systems of the present invention provide the user with direct operational control over the diffusion capabilities and diffusion rate of the device. Force applied to the dispensing system causes a reservoir to rotate. Such rotation may be directly correlated to the amount of volatile material that contacts a wicking surface. The amount of volatile material that contacts the wicking surface, in conjunction with the material type of the wicking surface, directly influences the diffusion rate of the volatile material. The present disclosure provides new and non-obvious volatile material dispensing systems, which address one or more of the above issues.

SUMMARY OF THE INVENTION

According to one aspect of the invention, a volatile material dispensing system includes a housing having at least one opening in a sidewall thereof and at least one engagement member extending from the housing. The volatile material dispensing system further includes a base adapted to interact with the housing, wherein the base includes a mechanical assembly. A reservoir contains a volatile material, wherein the reservoir rotates from a first position to a second position when the at least one engagement member contacts the mechanical assembly.

According to another aspect of the invention, a reservoir for a volatile material dispensing system includes a base having a sidewall extending therefrom. A film with a wicking surface extends over the sidewall to enclose a volatile material within the base and the sidewall. A pair of extension members are disposed on opposing sides of at least one of the base and the sidewall. The reservoir is designed to mechanically rotate from a first position into a second position about the extension members in response to an external force applied to the reservoir.

According to a different aspect of the invention, a reservoir for a volatile material dispensing system includes a base having a sidewall extending therefrom. A wicking surface extends over the sidewall to enclose a volatile material within the base and the sidewall. At least one extension member extends from the reservoir. The reservoir rotates about an axis formed by the extension member between a first operational state and a second operational state.

BRIEF DESCRIPTION OF THE DRAWINGS

FIG. 22 is a side isometric view of the volatile material dispensing system of FIG. 21 shown in a first operational state;

FIG. 23 is a side isometric view of the volatile material dispensing system of FIG. 21 shown in a second operational state;

FIG. 24 is a side isometric view of the volatile material dispensing system of FIG. 21 shown in an intermediate operational state;

FIG. 25A is a schematic view of the volatile material dispensing system of FIG. 13 shown in a passive state;

FIG. 25B is a schematic view of the volatile material dispensing system of FIG. 15 shown in an intermediate boost state;

FIG. 25C is a schematic view of the volatile material dispensing system of FIG. 14 shown in a boost state; and FIG. 26 is a graphical representation of various dispensing states of the volatile material dispensing system disclosed herein.

DETAILED DESCRIPTION OF THE DRAWINGS

Figure 1:
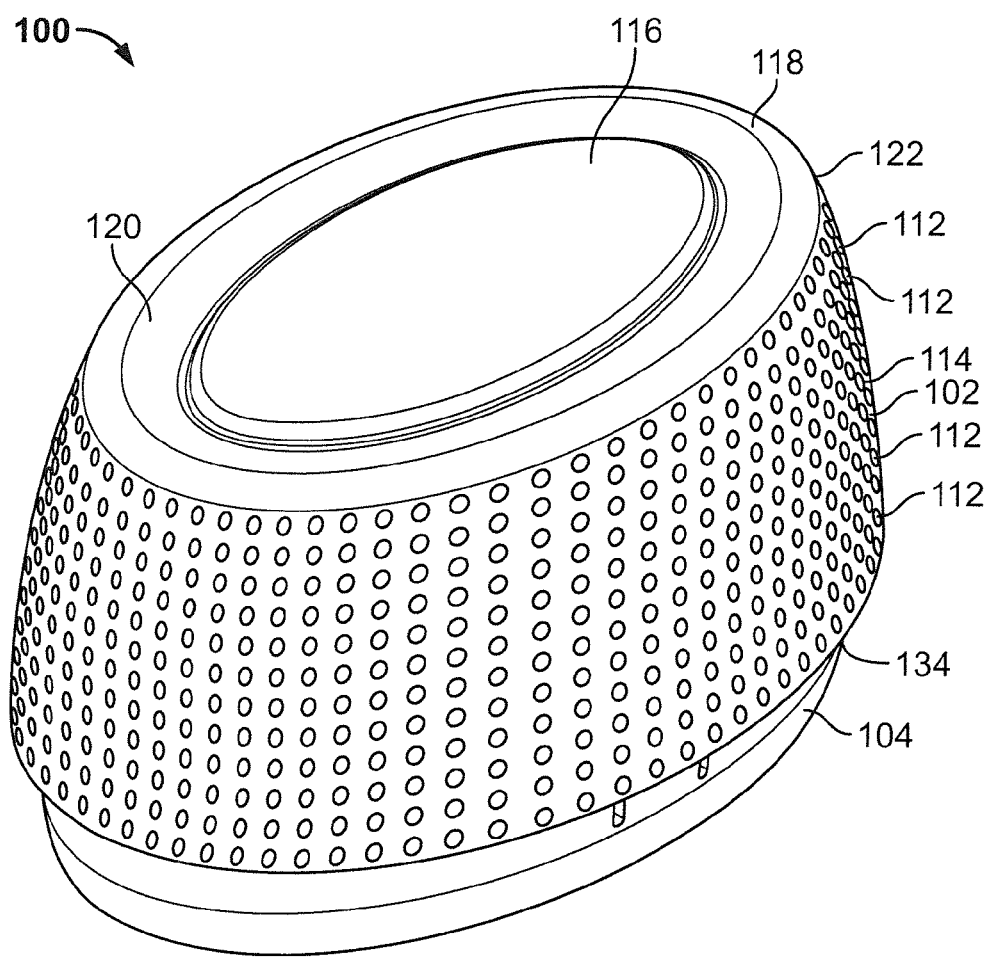
FIG. 1 is a top isometric view of a first embodiment of a volatile material dispensing system including a housing and a base.

As generally depicted in FIGS. 1-15, a volatile material dispensing system 100 comprises an elongate oval housing 102 releasably attached to a similarly shaped oval base 104. As shown in FIG. 9, a volatile material 106 is disposed in a reservoir 108 inside of the housing 102 and is supported by a mechanical assembly 110 (see FIG. 12) designed to rotatably position the reservoir 108 into a variety of operating conditions. The diffusion rate of the volatile material 106 changes when a user applies an external force to portions of the volatile material dispensing system 100, as will be described hereinbelow.

With reference to FIG. 1, the housing 102 includes a plurality of openings 112 disposed in a sidewall 114 thereof. Although a plurality of openings 112 are depicted, any number of openings 112 may be included in the volatile material dispensing system 100. Preferably, the housing 102 and/or base 104 includes at least one opening to allow the volatile material 106 to escape therefrom. The plurality of openings 112 may be provided around the entirety of the sidewall 114 of the housing 102 or only over a portion thereof. The plurality of openings 112 are depicted as circular in the embodiment shown in FIG. 1, but may comprise other shapes and sizes as known in the art.

The housing 102 further includes a control mechanism provided in the form of an oval button 116 disposed in an upper surface 118 thereof. In one embodiment, the button 116 is integral with the upper surface 118 (see FIG. 1). A slightly angled portion 120 of the upper surface 118 circumscribes the button 116 adjacent an edge 122. The angled portion 120 extends around the circumference of the button 116 and is adapted to guide a user's fingers toward the button 116. The button 116 protrudes upwardly above a plane formed by the upper surface 118 of the housing 102. The button 116 may be integral such that the button 116 does not physically separate from the housing 102. In this embodiment, the button 116 preferably provides a visual indicator of an appropriate area for a user to contact when the user desires to adjust the diffusion rate of the volatile material 106. Alternatively, the housing 102 may include a continuous upper surface 118 such that a separate button 116 is not distinguishable therefrom.

Figure 4:
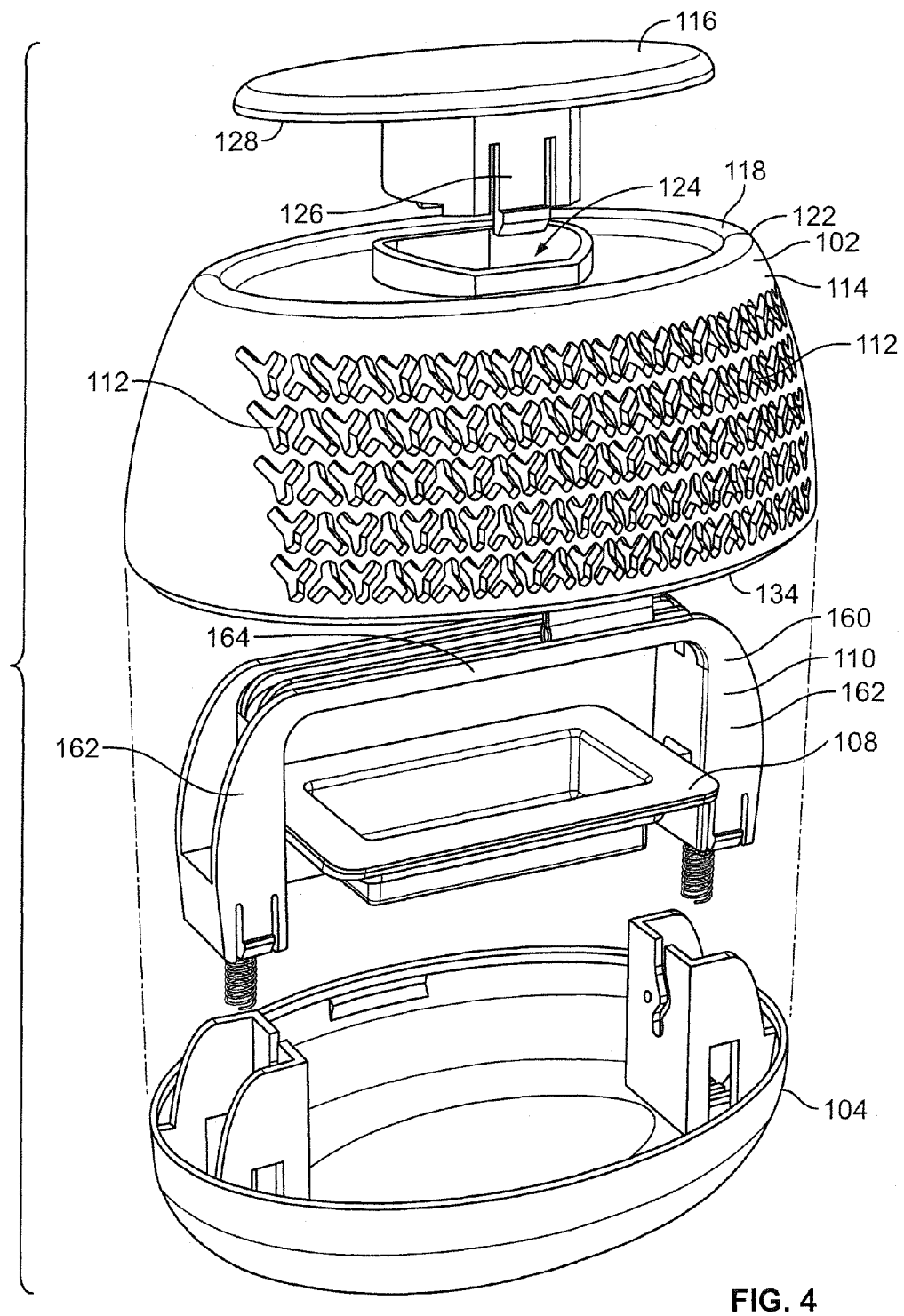
FIG. 4 is an exploded isometric view of a different embodiment of a volatile material dispensing system.

In an alternative embodiment shown in FIG. 4, the button 116 extends upwardly through an aperture 124 disposed in the upper surface 118 that is spaced interiorly from the edge 122 of the upper surface 118. The button 116 includes opposing latches 126 extending from an underside 128 thereof. The latches 124 may releasably lock onto internal portions (not shown) of the housing 102 to retain the button 116 in a depressed position. When depressed, the button 116 is in communication with the mechanical assembly 110 disposed inside of the housing 102. Although depicted as oval, the housing 102 and/or button 116 may comprise other shapes and sizes, for example square, rectangular, circular, and the like.

Figure 2:
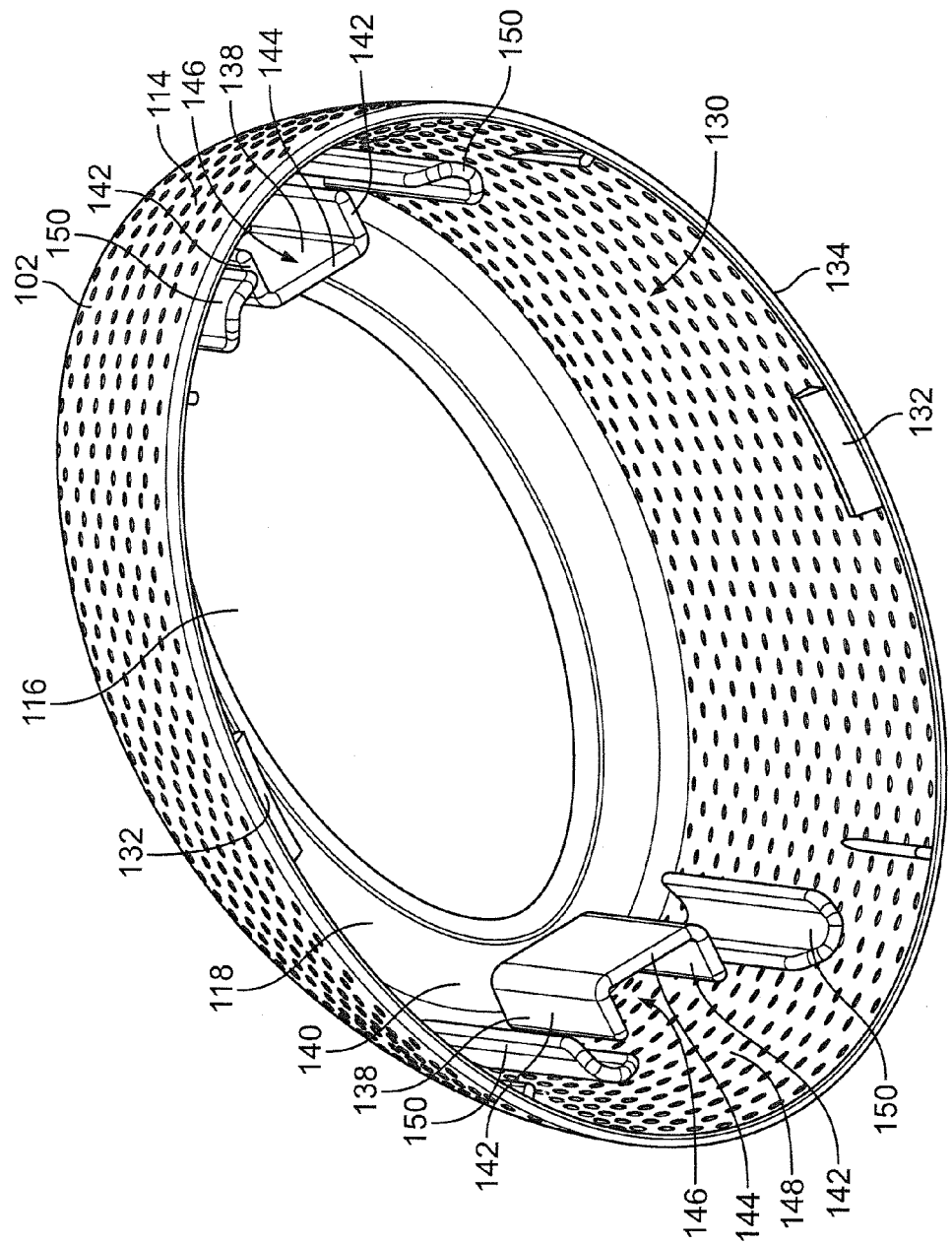
FIG. 2 is bottom isometric view of the housing of FIG. 1.

Now turning to FIG. 2, an interior portion of the housing 102 forms a compartment 130 that is adapted to substantially hide internal components of the dispensing system 100. The sidewall 114 of the housing 102 includes a plurality of resilient snaps 132 that extend inwardly from the sidewall 114 adjacent a lower edge 134 of the housing 102. The resilient snaps 132 are designed to releasably engage corresponding undercuts 136 (see FIGS. 5 and 6) disposed on the base 104 to retain the housing 102 on same.

The button 116 of the housing 102 and/or other portions of the housing 102 are in communication with the mechanical assembly 110. The mechanical assembly 110 comprises various components that are in communication with each other that act to translate a downward force applied on the housing 102 and/or button 116 into a rotational force that rotates the reservoir 108 holding the volatile material 106.

In one embodiment, portions of the mechanical assembly are provided in the form of one or more C-shaped elongate engagement members 138 (see FIGS. 2 and 3) that extend from an interior surface 140 adjacent the button 116. When a substantially downward force is applied to the button 116 and/or other portions of the housing 102, the engagement members 138 act on other portions of the mechanical assembly 110 disposed in the base 104. In a different embodiment, the engagement members 138 are integrally formed and extend from any portion of the housing 102, such as the button 116. In still another embodiment, the engagement members 138 comprise separate components that are positioned adjacent the interior surface 140 of the button 116. It is envisioned that the engagement members 138 may be provided in mechanical communication with the housing 102 and/or button 116 in other ways as known in the art.

Figure 3:
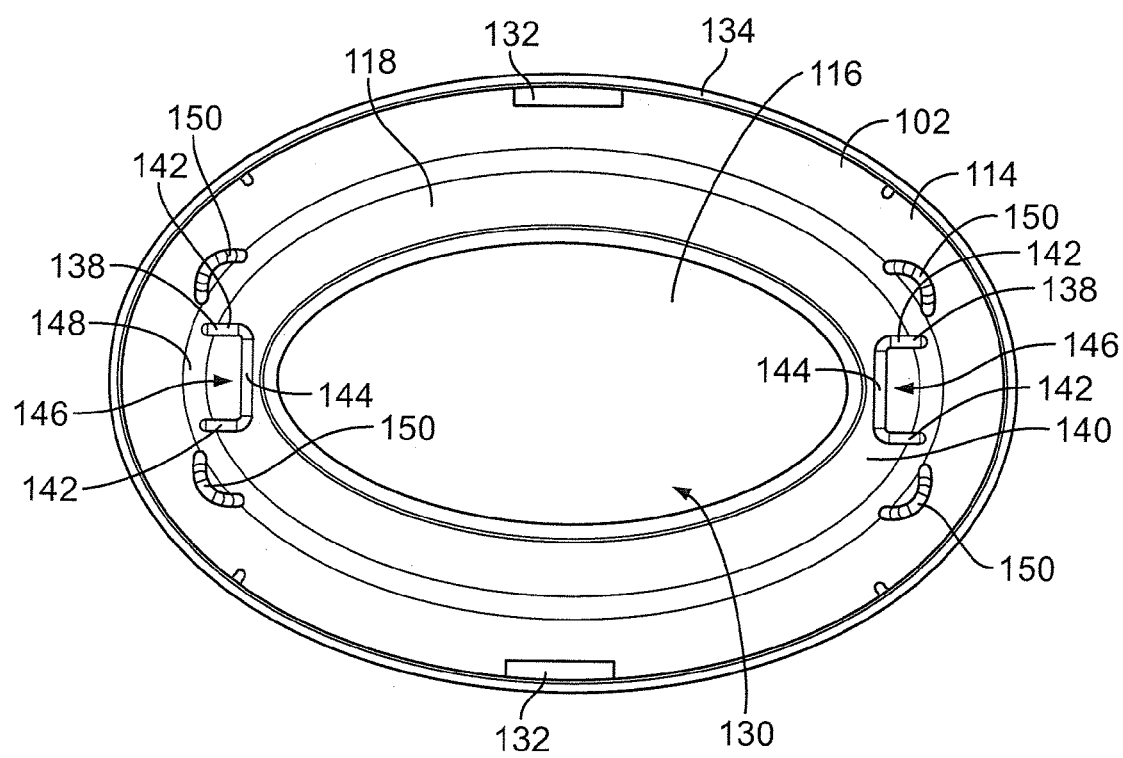
FIG. 3 is a bottom plan view of the housing of FIG. 1.

Still referring to FIGS. 2 and 3, the engagement members 138 of this embodiment include two opposing end walls 142 connected by an elongate sidewall 144. An opening 146 is provided in each of the engagement members 138 and is defined by the end walls 142, the sidewall 144, and an interior surface 148 of the sidewall 114 of the housing 102. A plurality of curved support members 150 are disposed along and extend from the interior surface 148 of the housing 102 adjacent the end walls 142 of each of the engagement members 138. The support members 150 at least partially restrict the downward movement of the housing 102 when the housing 102 is being pressed downwardly onto the base 104, as will be described in more detail hereinbelow. The support members 150 additionally provide structural stability and integrity to the housing 102.

In a different embodiment shown in FIG. 4, portions of the mechanical assembly 110 are provided in the form of an engagement member 160. The engagement member 160 of this embodiment includes two curved opposing end pieces 162 integrally connected to each other by an elongate connector piece 164. The engagement member 160 operates in a similar manner as the engagement members 138 in that portions of the housing 102 and/or button 116 interact with the engagement member 160 to force same downwardly to rotate the reservoir 108 and control the diffusion rate of the volatile material 106. It is envisioned that the mechanical assembly 110 could be constructed in various ways to accomplish the rotation of the adjustable reservoir 108 as described in more detail hereinbelow.

Figure 5:
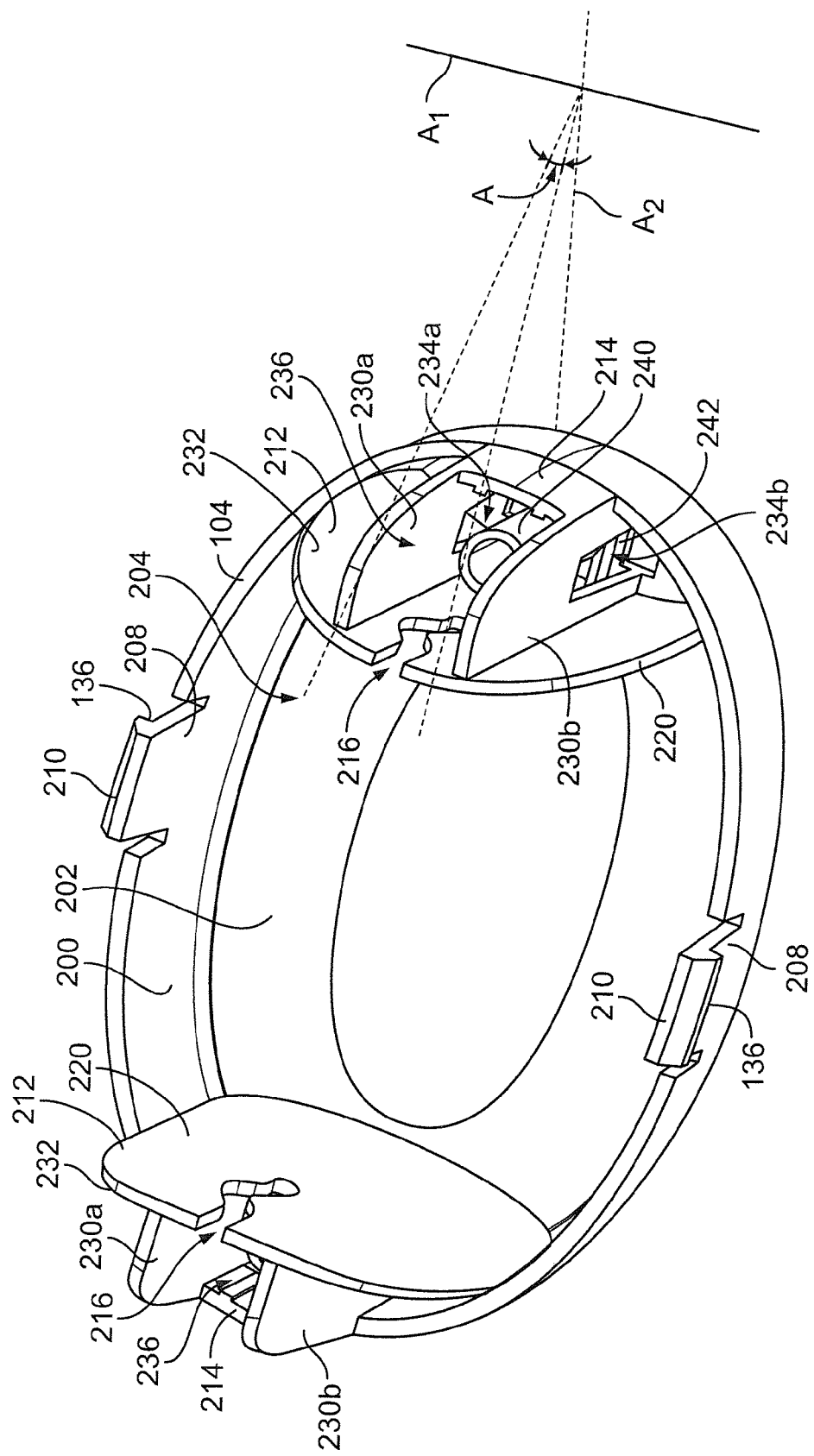
FIG. 5 is a top isometric view of the base of FIG. 1.
Figure 6:
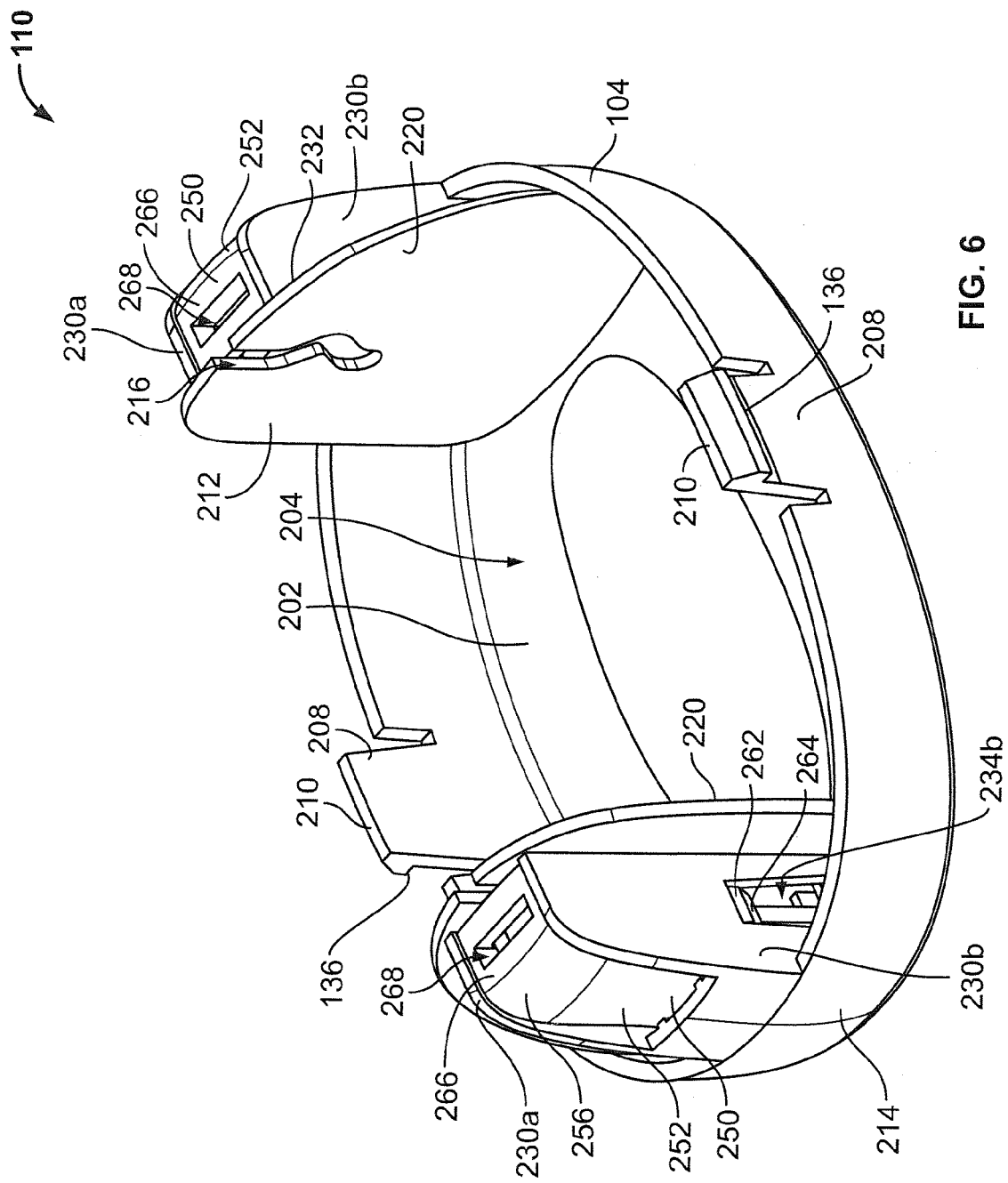
FIG. 6 is a side isometric view of the base of FIG. 5 further including cover members disposed therein.

Now turning to FIGS. 5 and 6, the housing 102 is adapted to snap-fit onto the base 104 of the volatile material dispensing system 100. The base 104 is substantially oval and includes a sidewall 200 that extends upwardly from a bottom surface 202. The bottom surface 202 is preferably substantially flat so that the volatile material dispensing system 100 may rest in an upright position when disposed on a flat support surface, such as, for example, a counter, ledge, coffee table, or bathroom surface. The bottom surface 202 and sidewall 200 of the housing 102 define a receiving compartment 204 for a refill unit 206. The refill unit 206 comprises the reservoir 108 with the volatile material 106 disposed therein (see FIG. 9), as will be described in more detail hereinbelow.

Still referring to FIGS. 5 and 6, a plurality of flexible prongs 208 extend upwardly from the sidewall 200 on opposing sides of the compartment 204. The prongs 208 each include corresponding undercuts 136 disposed adjacent top edges 210, respectively, which are designed to releasably interact with the resilient snaps 132 of the housing 102. Although a snap/undercut system is disclosed, it is envisioned that, for some embodiments, the housing 102 and base 104 may be releasably retained via other mechanisms as known in the art, such as, for example, an interference fit, an adhesive, and the like. In one embodiment, the housing 102 and the base 104 are integral such that the consumer is unable to access the internal components and the volatile material dispensing system 100 is adapted for a single-use. In another embodiment, the housing 102 and base 104 are separate and the volatile material dispensing system 100 may be reutilized and/or refilled when the volatile material 106 has been fully used or it is otherwise desired to change the refill unit 206.

As best seen in FIG. 5, the base 104 further includes a plurality of support walls that are adapted to support portions of the mechanical assembly 110. In particular, a pair of curved walls 212 each extend upwardly from the bottom surface 202 at opposing ends 214 of the base 104. The curved walls 212 each include a curved slot 216 disposed therethrough that extends downwardly from a central portion of the curved walls 212 to a distance of about halfway of the entire height of the curved wall 212. The slot 216 is designed to facilitate the rotation of the reservoir 108 that holds the volatile material 106 when the housing 102 and/or button 116 is engaged by a user. In the embodiment shown, the specific angling of the slot 216 is provided to rotate the reservoir 108 such that the volatile material 106 is diffused in a passive diffusion state (see FIG. 13) to an active (boost) diffusion state (see FIG. 14). It is envisioned that other notches and/or angling may be incorporated to allow for partial rotation of the reservoir 108 such that a variety of operating conditions may be accomplished through the mechanical interaction between the housing 102, the button 116 and the mechanical assembly 110 (see e.g., FIG. 15).

Two angled walls 230a, 230b extend outwardly from a rear surface 232 of each of the curved walls 212. The angled walls 230a, 230b each include a rectilinear slot 234a, 234b disposed therein that extends over a length of about half of the height of the angled walls 230a, 230b. The slots 234a, 234b extend through the entirety of the angled walls 230a, 230b. As best seen in FIG. 5, each of the angled walls 230a, 230b extend outwardly from the curved walls 212 such that the angled wall 230a and the angled wall 230b extend toward one another and the respective end 214 of the base 104. An angle A (see FIG. 5) is formed between angled wall 230a and angled wall 230b with respect to axes $A_1$ and $A_2$, and is between about 10 degrees to about 90 degrees, more preferably between about 20 degrees to about 75 degrees, and most preferably about 35 degrees.

Figure 12:
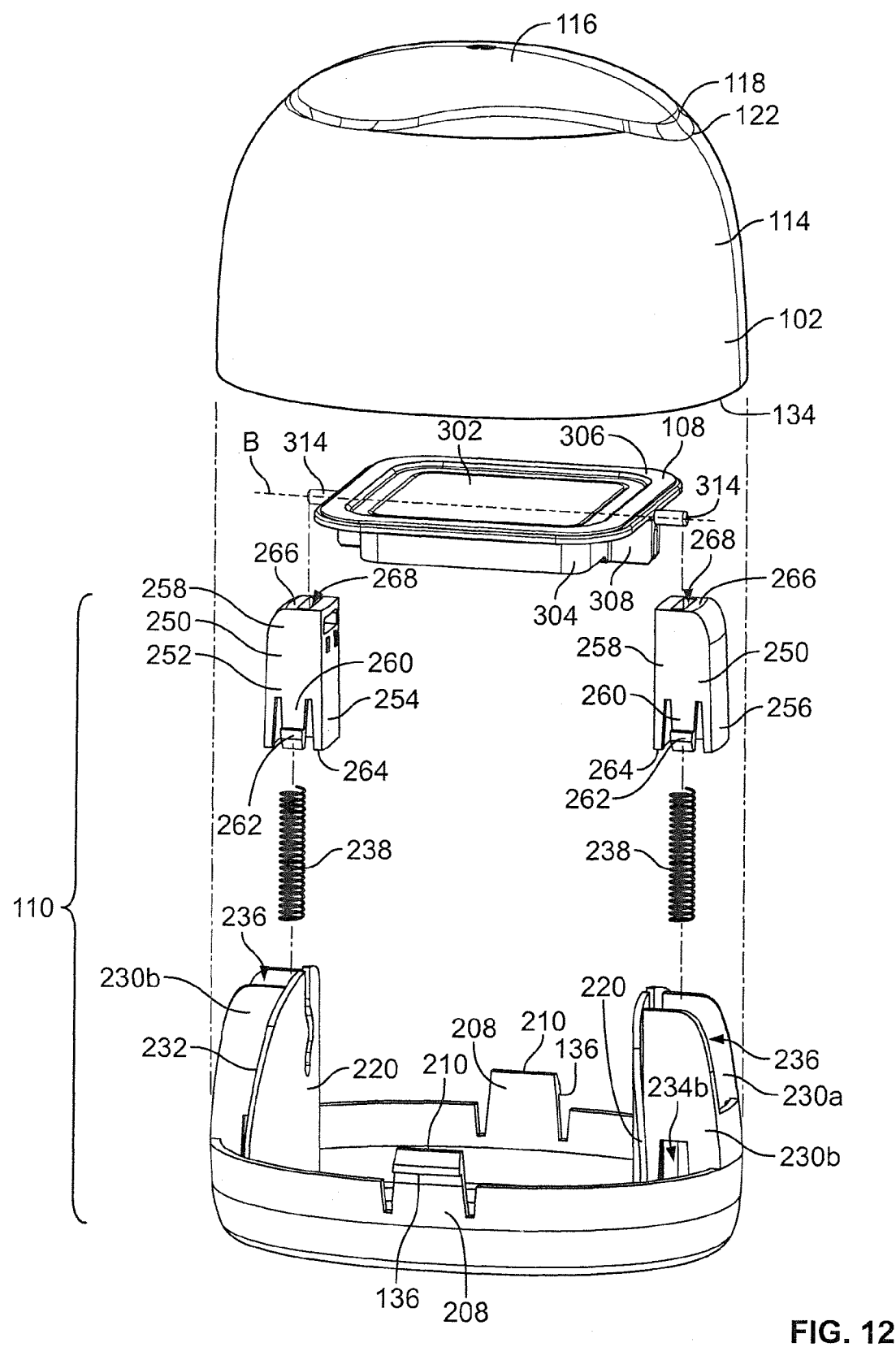
FIG. 12 is an exploded isometric view of the volatile material dispensing system of FIG. 1.
Figure 13:
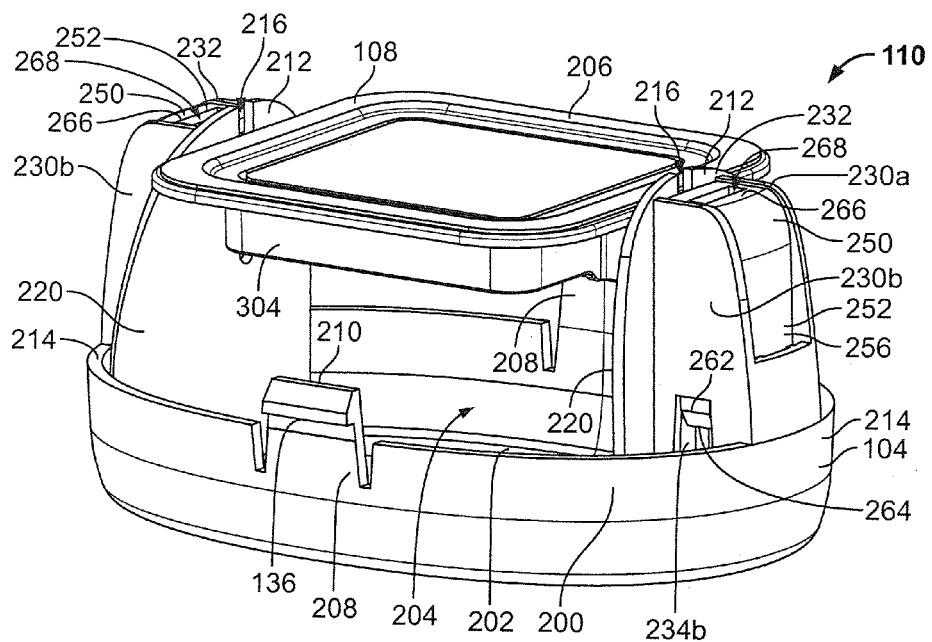
FIG. 13 is a side isometric view of the volatile material dispensing system of FIG. 1 shown in a first operational state with the housing removed therefrom for purposes of clarity.
Figure 14:
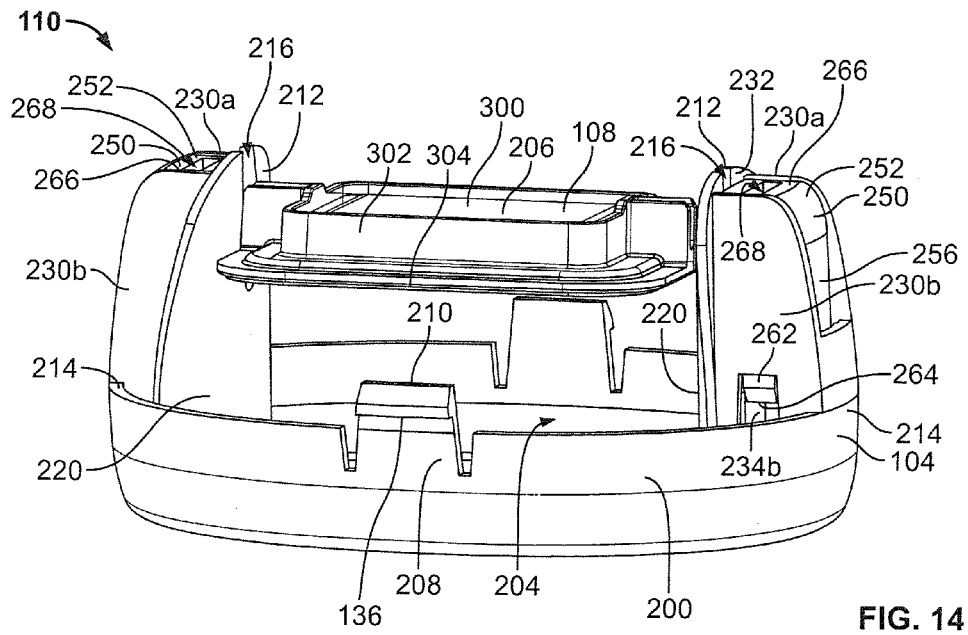
FIG. 14 is a side isometric view of the volatile material dispensing system of FIG. 1 shown in a second operational state with the housing removed therefrom for purposes of clarity.

As best seen in FIG. 12, a gap 236 is created between angled walls 230a, 230b and includes a spring 238 provided therebetween. The spring 238 is supported by a cylindrical member 240 (see FIG. 5) that extends upwardly from the bottom surface 202 of the base 104. A plurality of elongate flanges 242 protrude upwardly from the bottom surface 202 and are disposed around the cylindrical member 240. The flanges 242 are adapted to provide structural integrity to the bottom surface 202 of the base 104.

Figure 7:
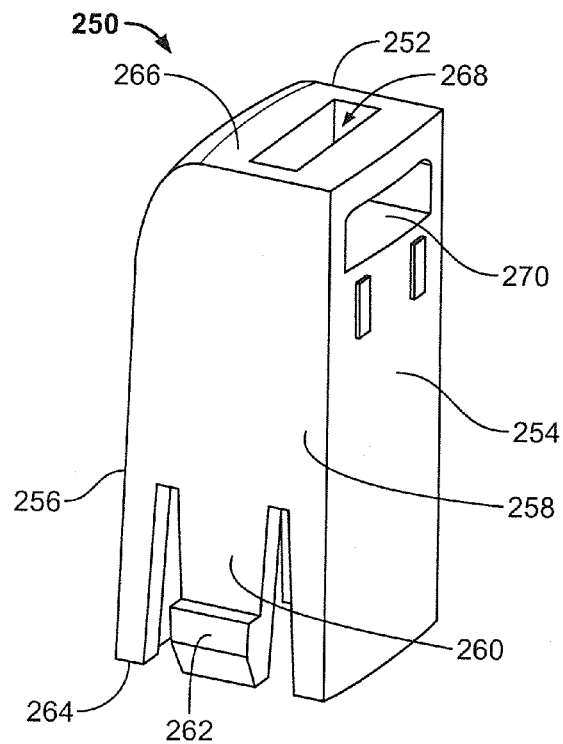
FIG. 7 is a top isometric view of one of the cover members of FIG. 6.
Figure 8:
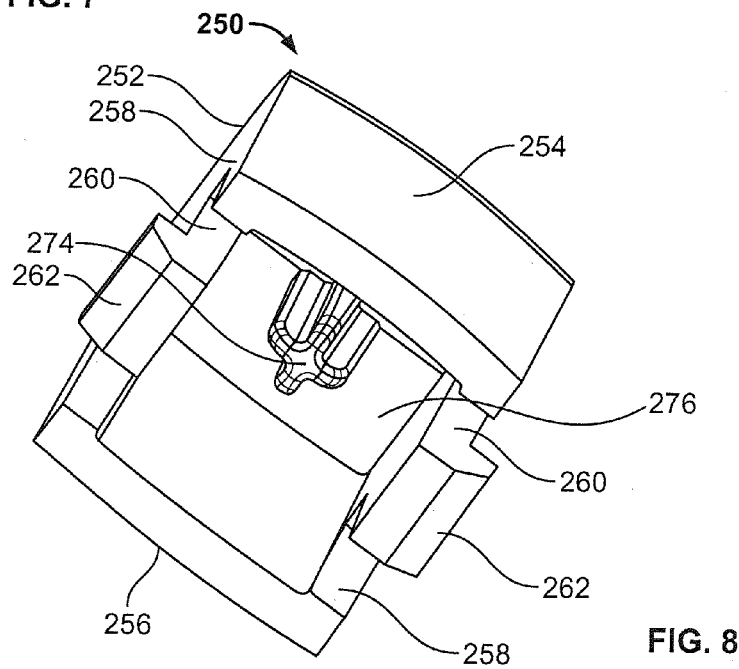
FIG. 8 is a bottom isometric view of one of the cover members of FIG. 6.
Figure 9:
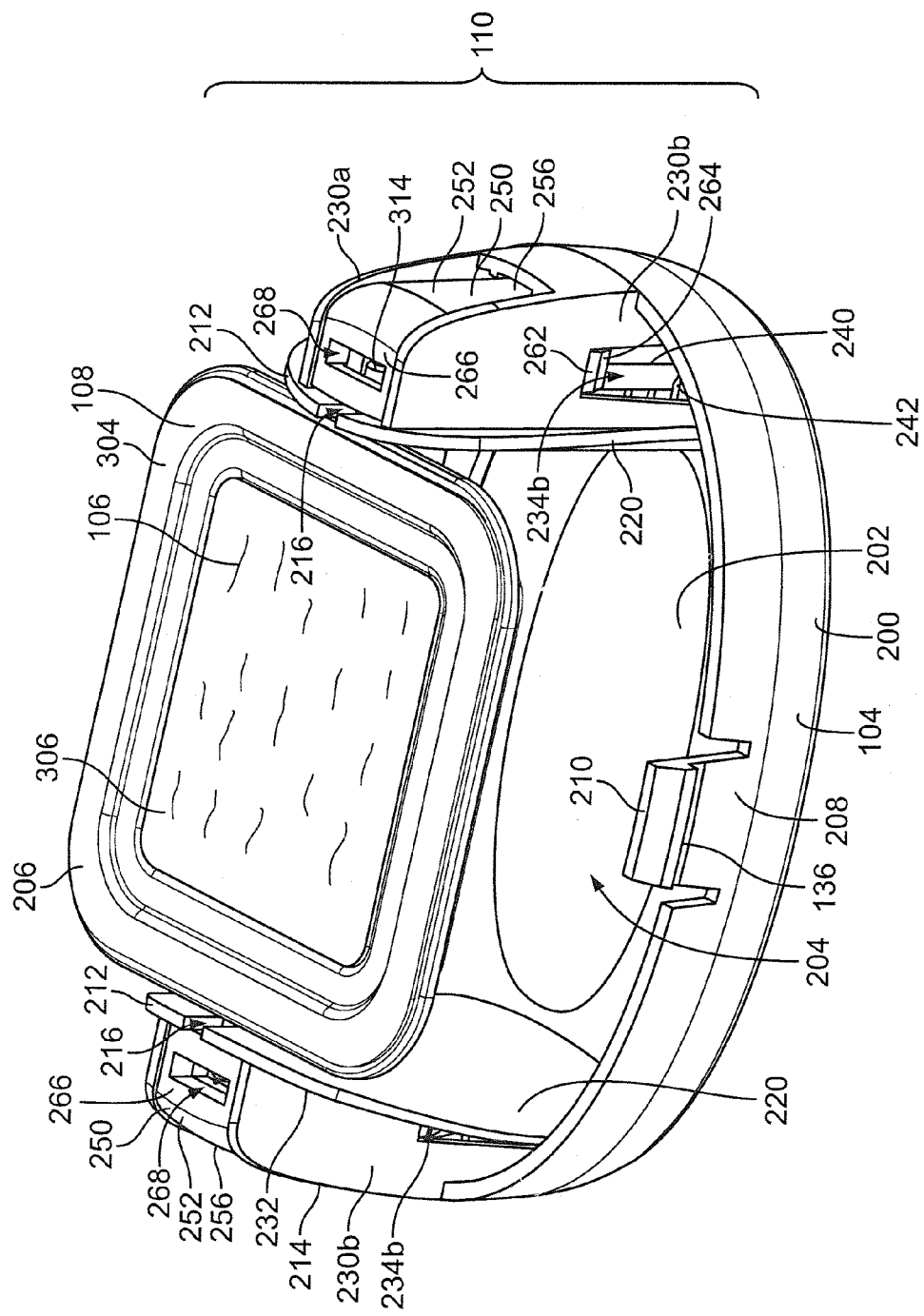
FIG. 9 is a top isometric view of the base of FIG. 6 further including a reservoir.
Figure 10:
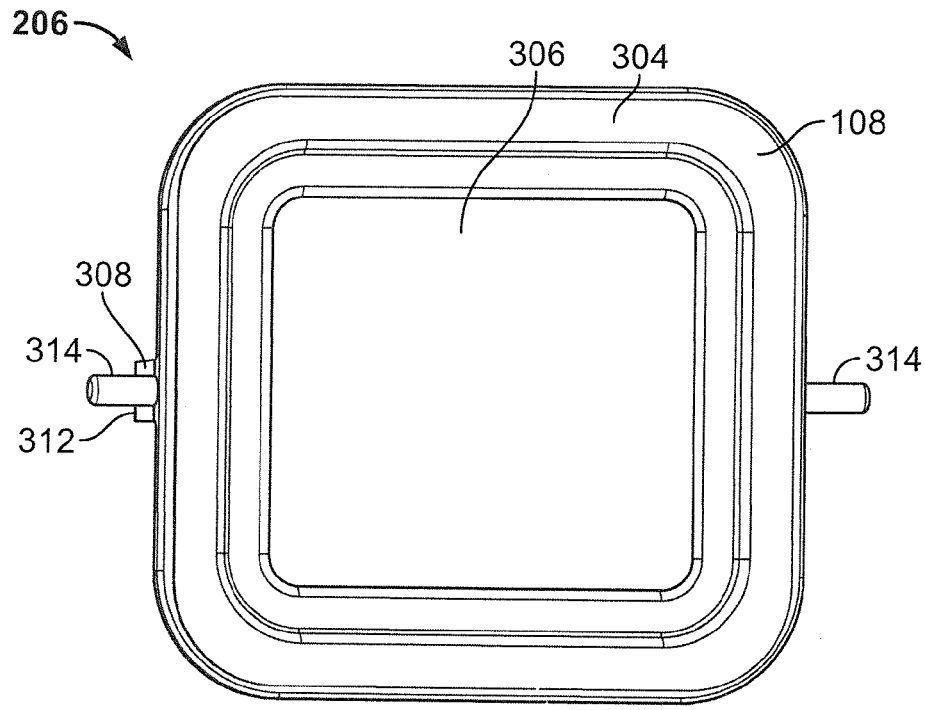
FIG. 10 is a top isometric view of the reservoir of FIG. 9.

As depicted in FIGS. 7 and 8, the spring 238 is adapted to be enclosed by a cover member 250. Each cover member 250 includes an elongate body 252 defined by a slightly curved front surface 254 and a back surface 256 connected by two opposing sidewalls 258. The sidewalls 258 are interrupted by resilient tabs 260 extending from opposing sides thereof. Each tab 260 includes a stepped protrusion 262 that extends outwardly adjacent a bottom edge 264 thereof. The stepped protrusions 262 are designed to interact with portions of the elongate slots 234a, 234b (see FIGS. 6 and 13) disposed in the angled walls 230a, 230b. The cover members 250 each include a top surface 266 that is truncated by an elongate orifice 268 disposed adjacent a top edge. The front surface 254 includes an opening 270 adjacent the orifice 268.

With specific reference to FIG. 8, the body 252 of the cover members 250 are hollow and each include a cross-shaped cylindrical protrusion 274 extending from an interior surface 276 thereof. The protrusions 274 are designed to interact with and support a top section of the spring 238. The cylindrical protrusion 274 that extends from the cover member 250, in combination with the cylindrical member 240 disposed on the bottom surface 202 of the base 104, assist in securing the spring 238 in an upright position.

The cover members 250 are designed to be slideably held within the slots 234a, 234b of the angled walls 230a, 230b such that the spring 238 is secured in an upright position. The cover members 250 are designed to slide in a downward direction when a downward force interacts thereon. The sliding of the cover member 250 compresses the spring 238, which is held within the cover member 250. When downward force is removed from the cover member 250, the spring 238 decompresses and forces the cover member 250 to slide upwardly such that the stepped protrusions 262 of the resilient tabs 260 interact with portions of the elongate slots 234a, 234b disposed in the angled walls 230a, 230b until the stepped protrusions 262 catch on an upper edge of the slots 234a, 234b.

Now turning to FIGS. 9-12, the mechanical assembly 110 is adapted to support the reservoir 108 that holds the volatile material 106. The reservoir 108 includes a substantially rectangular base 300 having a sidewall 302 extending upwardly therefrom. The sidewall 302 terminates at a flared flange 304 that circumscribes and extends outwardly therefrom. A wicking surface 306 extends across the flange 304 and encloses the volatile material 106 within the reservoir 108. A non-permeable substrate (not shown) may be optionally applied to cover the wicking surface 306 to prevent the volatile material 106 from diffusing prior to use. The substrate is preferably removed from the wicking surface 306 prior to use.

The wicking surface 306 preferably comprises a film made from polymers, such as polyethylene. In one embodiment, the film comprises a high molecular weight polyethylene. The film optionally further includes various additives, such as, carbon, precipitated silica, and the like. Other films suitable for use as the wicking surface 306 include, for example, the Teslin SP400 or SP401 membranes made by PPG Industries, and the DURALIFE® and the Flatsheet Membrane made by Daramic. The films suitable for use may optionally be flat, ridged, and/or textured on one and/or both sides of the film. The films suitable for use with the reservoir 108 preferably comprise a thickness dimension of about 100 microns to about 1000 microns, or about 300 microns to about 700 microns, or about 600 microns (not including thickness that may be added due to ridges or texture). In one embodiment, the film thickness is greater than or equal to about 20 microns. In one particular embodiment, the film thickness is about 20 microns. In another embodiment, the film thickness is about 50 microns. In still a further embodiment, the film thickness is about 100 microns. In yet a different embodiment, the film thickness is about 200 microns.

The films useful with the volatile material dispensing system 100 herein further include a residual oil content, which affects the porosity of the film and/or diffusion of the volatile material through the film. The residual oil content is preferably less than about 20%, and in another embodiment less than about 16%, in a different embodiment less than about 10%, in another embodiment less than about 5%, and in still another embodiment less than about 1%. In one embodiment, the residual oil content is between about 1% and about 20%.

The films useful with the volatile material dispensing system 100 herein further include a porosity parameter selected according to the desired diffusion rate. The porosity of the film is preferably between about 10% to about 90%, and more preferably between about 30% to about 80%, and most preferably between about 40% to about 70%.

The wicking surface 306 extends across and seals the reservoir 108. The wicking surface 306 preferably provides a surface area for diffusion of about 100 cm$^2$ to about 1000 cm$^2$, more preferably about 300 cm$^2$ to about 700 cm$^2$, and most preferably about 500 cm$^2$.

Figure 11:
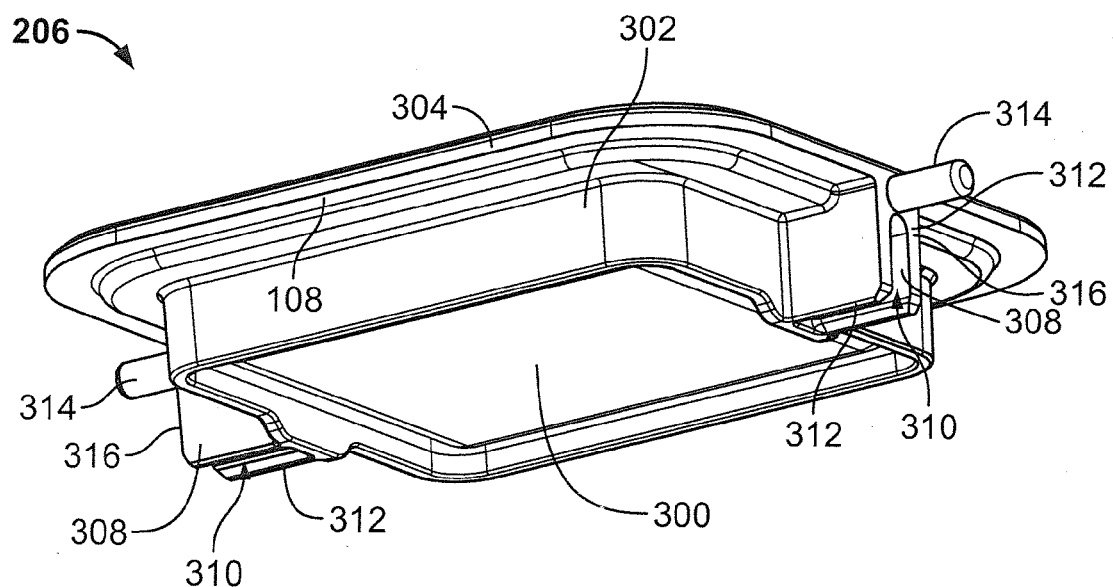
FIG. 11 is a bottom isometric view of the reservoir of FIG. 10.

With reference to FIG. 11, extension members in the form of substantially rectangular protrusions 308 extend outwardly from opposing ends of the sidewall 302 of the reservoir 108. The protrusions 308 are interrupted by an elongate slot 310 extending therethrough. Each slot 310 terminates at two opposing endwalls 312, which are slightly tapered.

Turning again to FIGS. 9-11, cylindrical protuberances 314 extend outwardly from a distal end 316 of each of the protrusions 308. The protuberances 314 are adapted to extend through the opening 270 of the front surface 254 of the cover members 250 and to be supported thereby. In the present embodiment, the protuberances extend into the opening 270 a distance sufficient to place them beneath the orifices 268 within the top surface 266 of the cover members 250 (see FIG. 9). In one embodiment, portions of the engagement members 138 interact with the orifices 268 when downward force is applied to the housing 102 and/or button 116.

Prior to use, the housing 102 is preferably attached to the base 104 by lowering the housing 102 onto the base such that the engagement members 138 rest on portions of the cover members 250. Further, the support members 150 are slideably received in areas adjacent the slots 234a, 234b of the angled walls 230a, 230b. Releasable attachment is effected by inward flexing of the prongs 208 of the base 104 as the resilient snaps 132 of the housing 102 ride over the undercuts 136 to form a secure fit therebetween.

During a first operational state (see FIG. 13), the reservoir 108 is provided in a substantially horizontal position such that the volatile material 106 does not substantially contact the wicking surface 306. In this state, the volatile material 106 diffuses at a passive rate, i.e., diffusion at typical room conditions without elements that substantially increase or decrease the diffusion rate.

During a second operational (boost) state (see FIG. 14), the user of the volatile material dispensing device 100 applies a downward force to the housing 102 and/or button 116 to cause a series of mechanical interactions that ultimately result in the reservoir 108 rotating into a position different than the horizontal position of the first operational state. In particular, in one embodiment, when downward force is applied to the button 116, the engagement members 138 move downwardly and contact the cover members 250. In turn, the cover members 250 slide downwardly and compress the spring 238. At the same time, the stepped protrusions 262 of the resilient tabs 260 slideably interact with portions of the elongate slots 234a, 234b disposed in the angled walls 230a, 230b. As the cover members 250 move downwardly, the protuberances 314 that extend from the reservoir 108 are forced downwardly through the slot 216. The angling of the slot 216 forces the reservoir 108 to rotate about an axis B formed by the protuberances 314 (see FIG. 12). From the beginning of the rotation process to the end of the rotation process, the reservoir 108 is designed to rotate between about 20 degrees to about 180 degrees, more preferably between about 45 degrees to about 130 degrees, and most preferably between about 90 degrees to about 110 degrees.

With reference still to FIG. 12, when a force is removed from the housing 102, the engagement members 138 (see FIG. 2) move upwardly and cease contacting the cover members 250. The cover members 250 slide upwardly and the spring 238 opens into an extended position. The stepped protrusions 262 of the resilient tabs 260 slideably interact with top portions of the elongate slots 234a, 234b disposed in the angled walls 230a, 230b. The protuberances 314 that extend from the reservoir 108 move upwardly through the slot 216. The angling of the slot 216 forces the reservoir 108 to rotate about an axis B formed by the protuberances 314 back into the first operational state depicted in FIG. 13. Optionally, a lock or other mechanism (not shown) may be included to retain the reservoir 108 in one or more operational conditions.

Figure 15:
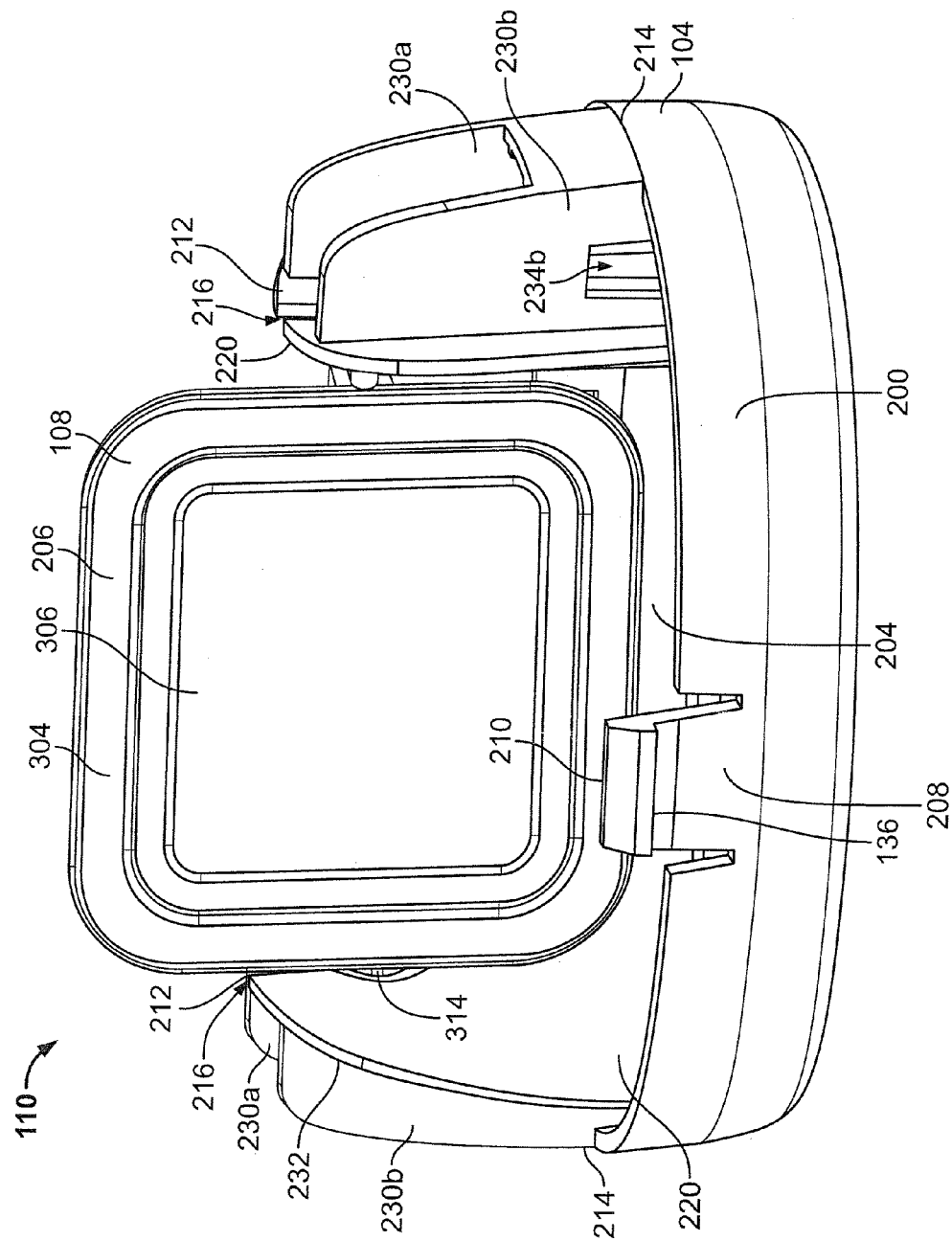
FIG. 15 is a side isometric view of the volatile material dispensing system of FIG. 1 shown in an intermediate operational state with the housing removed therefrom for purposes of clarity.

Optionally and/or additionally, one or more intermediate operational states may be provided for in the design of the volatile material dispensing system 100 (see FIG. 15). For example, in one embodiment, rotation of the reservoir 108 about 180 degrees may provide a boost of fragrance such that the volatile material 106 covers substantially the entirety of the wicking surface 306 and is diffused therefrom at a substantially increased rate. In comparison, rotation of the reservoir 108 about 120 degrees may provide for a boost less than that of the maximum boost because the volatile material 106 may cover a smaller portion of the wicking surface 306. In a different embodiment, the diffusion rate of the volatile material 106 through the wicking surface 306 is increased as soon as any amount of the volatile material 106 contacts the wicking surface 306 due to capillary action and spreading of the volatile material 106 over substantially the entirety of the wicking surface 306. As discussed hereinbelow, numerous factors influence the diffusion rate of the volatile material 106 with respect to the rotation of the reservoir 108 including at least the type and properties of the wicking surface, the type and properties of the volatile material 106, the degree of rotation of the reservoir 108 and other factors as known in the art.

Figure 16:
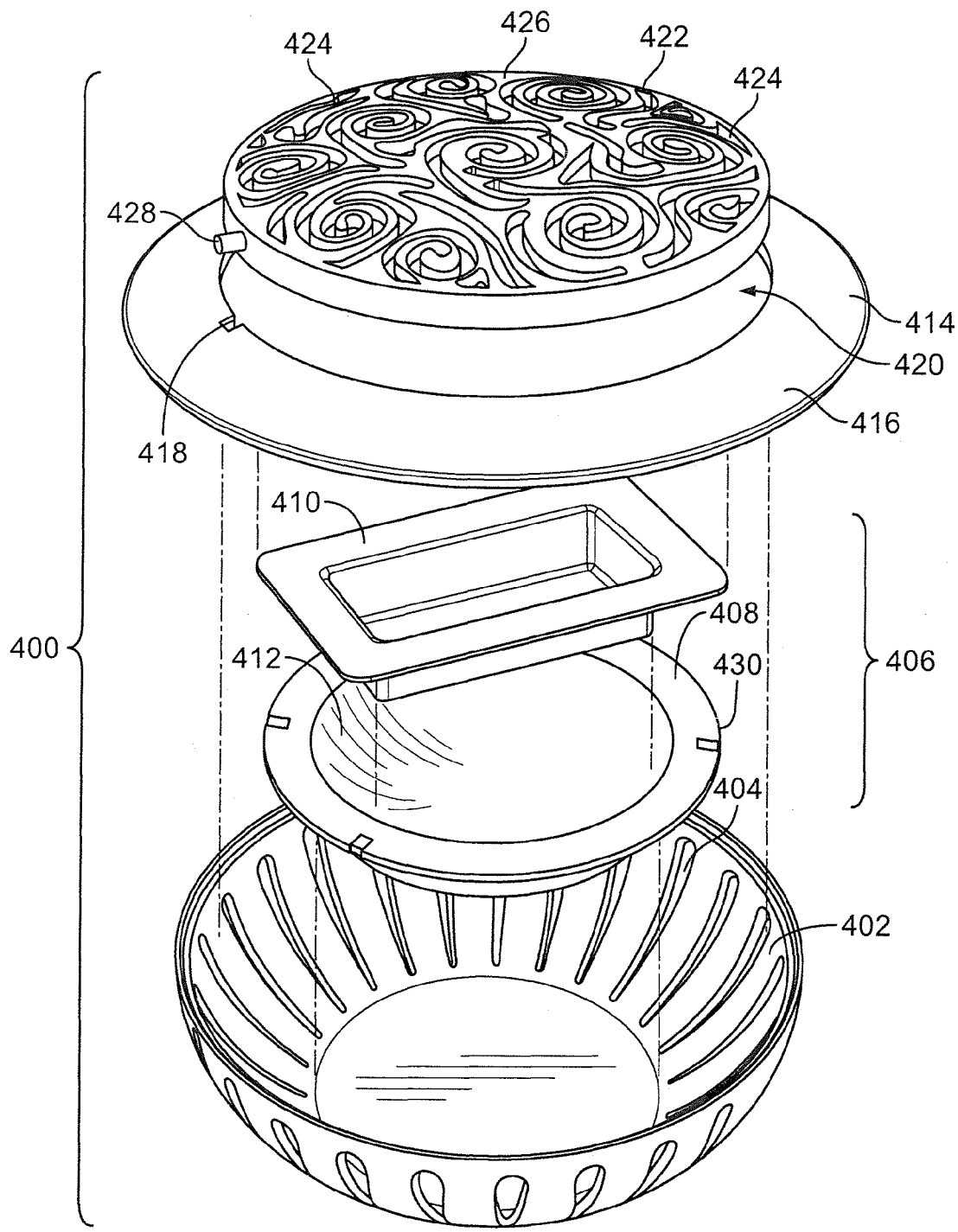
FIG. 16 is an exploded isometric view of a different embodiment of a volatile material dispensing system.
Figure 17:
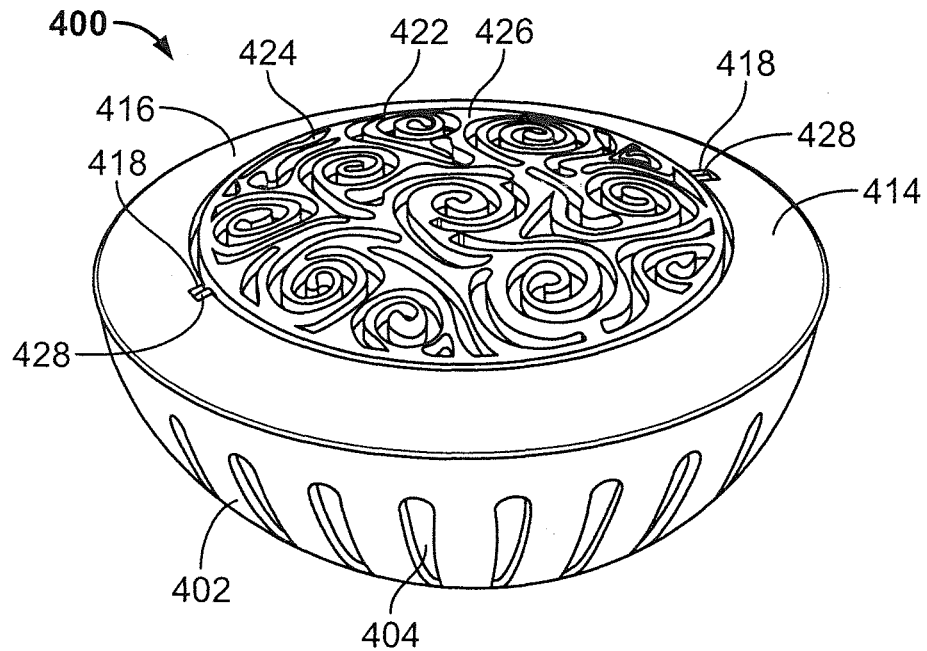
FIG. 17 is a side isometric view of the volatile material dispensing system of FIG. 16 shown in a first operational state.
Figure 18:
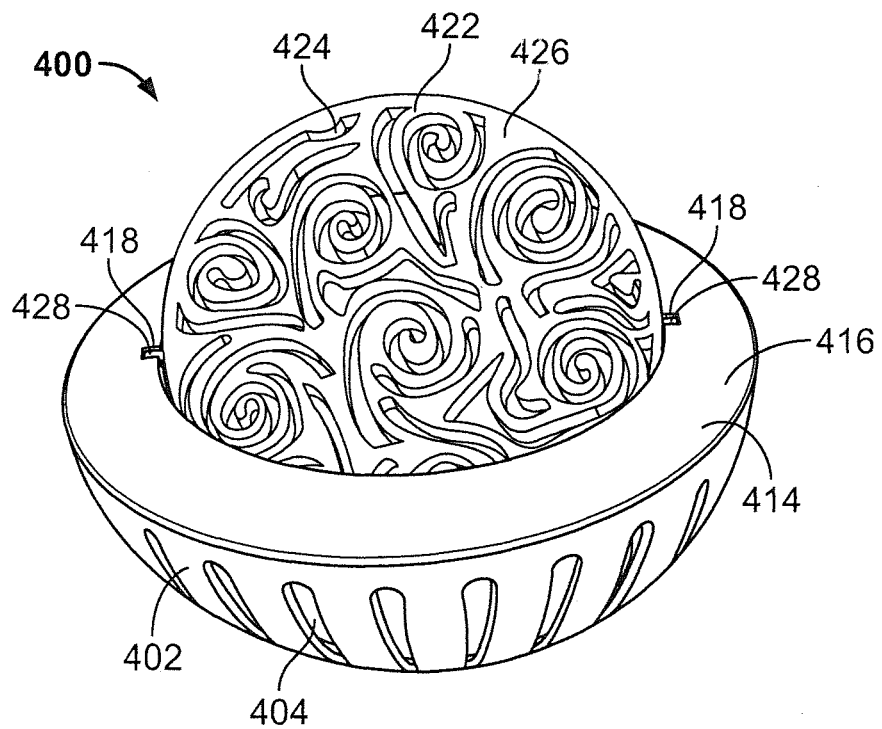
FIG. 18 is a side isometric view of the volatile material dispensing system of FIG. 16 shown in a second operational state.

Now turning to FIGS. 16-18, an alternative embodiment of a volatile material dispensing system 400 is depicted. The volatile material dispensing system 400 includes a bowl shaped base 402 having a plurality of orifices 404 extending therethrough. The base 402 is adapted to retain a refill assembly 406 that includes a similarly shaped bowl-shaped refill support plate 408 and a reservoir 410. The reservoir 410 is supported in the support plate 408 and disposed adjacent an interior surface 412. A circular collar 414 is provided and includes a slightly angled circular sidewall 416 with two notches 418 disposed in opposing sides thereof. The sidewall 416 defines an orifice 420 therein. The collar 414 is adapted to confine the reservoir 410 and the support plate 408 within the base 402. In the embodiment shown in FIGS. 16-18, the collar 414 attaches to the base 402 in an interference manner. However, it is envisioned that the collar 414 may be attached to the base 402 in other manners as is known in the art.

A circular cover 422 having a size similar to that of the orifice 420 of the collar 414 is designed to be retained therein. The cover 422 includes a plurality of openings 424 that extend through a surface 426 thereof. The cover 422 further includes cylindrical protrusions 428 extending from opposing sides thereof. The protrusions 428 are adapted to be retained within the notches 418 of the collar 414. The cover 422 further includes an undercut (not shown) on an interior side thereof that interacts with an outer edge 430 of the support plate 408 to retain same. A rotatable unit is formed by the combination of the support plate 408 and the cover 422, wherein the reservoir 410 is captured therebetween.

In use, a user applies downward force on portions of the cover 422. The downward force causes a rotatable unit (i.e., the cover 422, the reservoir 410, and the support plate 408) to rotate about the notches 418. In this way, the user is able to control the amount of diffusion that is desired. FIG. 17 depicts the volatile material dispensing system 400 in a passive state. FIG. 18 depicts the volatile material dispensing system 400 in a boost state. It should be apparent that any number of intermediate boost states may be accomplished depending on how much the user rotates the rotatable unit.

Figure 19:
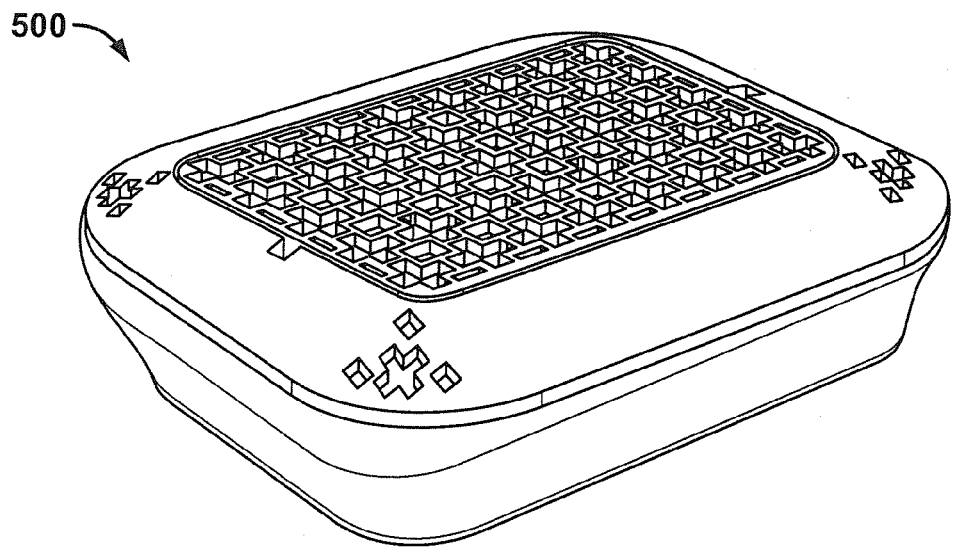
FIG. 19 is a side isometric view of an alternative embodiment of the volatile material dispensing system of FIG. 16 shown in a first operational state.
Figure 20:
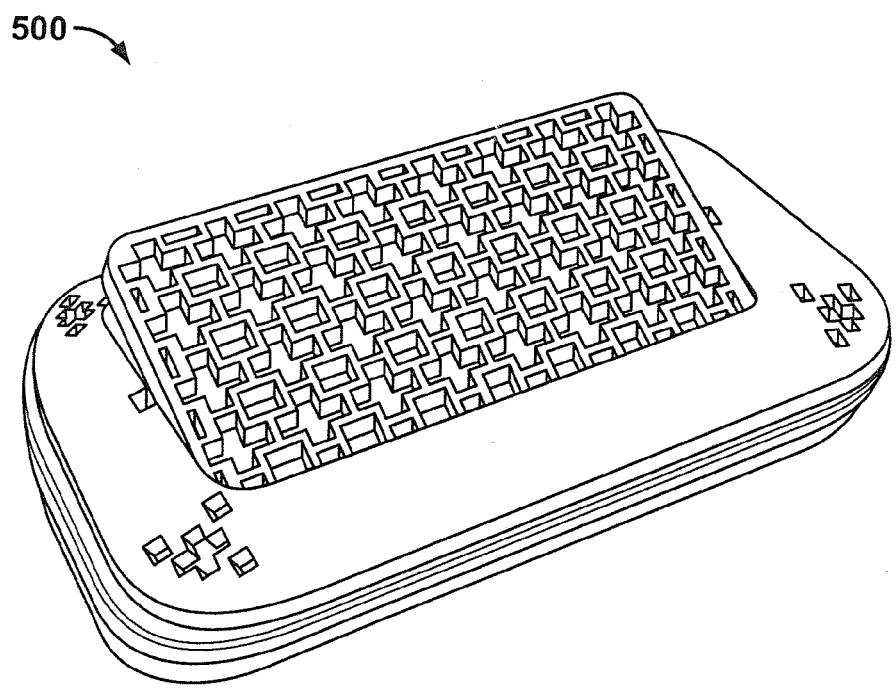
FIG. 20 is a side isometric view of the embodiment of the volatile material dispensing system of FIG. 19 shown in a second operational state.
Figure 21:
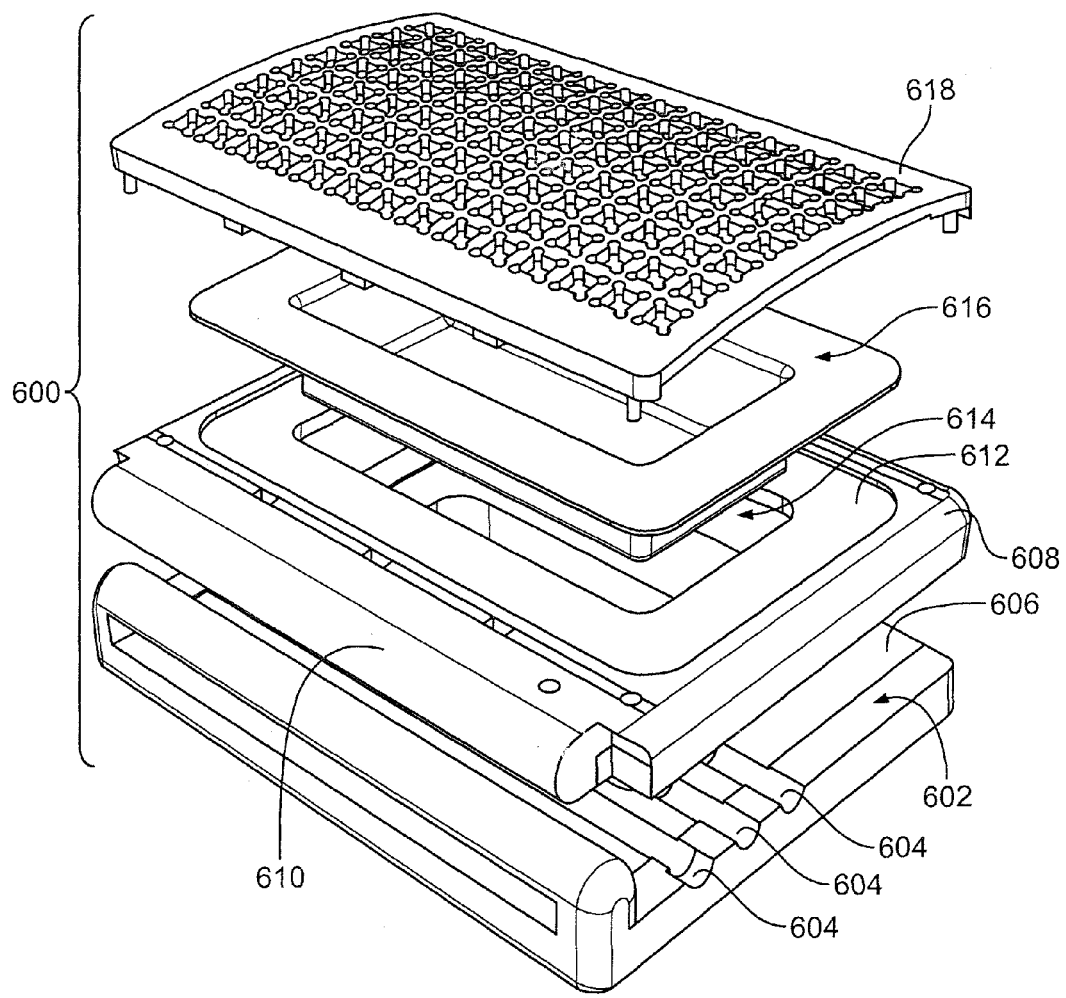
FIG. 21 is an exploded isometric view of a different embodiment of a volatile material dispensing system.

The shape of the volatile material dispensing system 400 may be circular, as shown in FIGS. 16-18 or may comprise other shapes. For example, a volatile material dispensing system 500 is depicted in FIGS. 19 and 20, which is operationally similar to the volatile material dispensing system 400 shown in FIG. 16-18, but instead comprises a substantially rectangular-shape.

Now turning to FIGS. 21-24, in a different embodiment, a volatile material dispensing system 600 is provided that also allows a user to manually control the diffusion rate of the volatile material. The volatile material dispensing system 600 includes a substantially rectangular base 602 having a plurality of grooves 604 disposed in an exterior surface 606 thereof. The grooves 604 extend longitudinally along the length of the exterior surface 606. A carrier 608 is hingedly attached to the base 602 at an end 610 thereof. The carrier 608 further includes a recess 612 disposed therein and a smaller orifice 614 that extends through the recess 612. The recess 612 and the orifice 614 are adapted to receive a reservoir 616 that holds a volatile material (not shown). A cover 618 is provided that attaches over the reservoir 616 to the carrier 608. Similar to other embodiments, the diffusion rate of the volatile material dispensing system 600 is adjusted by rotating the cover 618 from a passive state (see FIG. 22) to various intermediate states (FIGS. 23 and 24).

As depicted in FIGS. 25A-25C, the volatile material dispensing systems disclosed herein allow a user to control the diffusion rate of the volatile material 106 by rotating the reservoir 108 to adjust the amount of volatile material 106 that contacts the wicking surface 306. As shown in FIG. 25A, the reservoir 108 is oriented in a horizontal orientation with respect to the bottom surface 202 of the base 104 (as oriented in FIG. 13) and the volatile material 106 contacts a bottom surface 700 of the reservoir 108 and does not contact the wicking surface 306. In the operating condition shown in FIG. 25A, the volatile material 106 is diffused through the wicking surface in a passive manner.

As shown in FIG. 25B, the reservoir 108 is oriented at about a 90 degree angle with respect to the bottom surface 202 of the base 104 (as oriented in FIG. 15). The volatile material 106 contacts a portion of the bottom surface 700 of the reservoir 108, a side 202 of the reservoir 108, and a portion of the wicking surface 306. In the embodiment depicted, about 50% of the surface area of the wicking surface 306 is contacted by the volatile material 106. Although the volatile material 106 is depicted as contacting about 50% of the surface area of the wicking surface 306 in the intermediate operating condition, it should be appreciated that the amount of volatile material 106 that contacts the wicking surface 306 will decrease as the volatile material 106 is diffused. In the operating condition shown in FIG. 25B, the volatile material 106 is diffused through the wicking surface 306 in an intermediate boost state, whereby a portion of volatile material 106 is in direct contact with the wicking surface 306. In one embodiment, substantially the entirety of the wicking surface 306 may be in contact with the volatile material 106 due to wicking properties even if the reservoir 108 is oriented at about a 90 degree angle as shown in FIG. 15. In the present embodiment, the intermediate boost state diffuses the volatile material at a faster rate than that of the passive state shown in FIG. 25A, but at a lower diffusion rate than the boost state shown in FIG. 25C. In another embodiment, the diffusion rates of the boost states shown in FIGS. 25B and 25C may be substantially the same. Similarly to the other operating conditions, numerous factors may influence the diffusion rate of the volatile material 106 when the reservoir 108 is disposed in an intermediate position. For example, the time that the reservoir 108 is retained in the intermediate position, the type and properties of the wicking surface and volatile material, the degree of rotation, and other properties of the volatile material dispensing system 100 may influence the diffusion rate.

As depicted in FIG. 25C, the reservoir 108 is oriented at about a 180 degree angle with respect to the bottom surface 202 of the base 104 (see FIG. 14) and the volatile material 106 does not contact the bottom surface 700 of the reservoir 108. Rather, the volatile material 106 contacts the sides 702 of the reservoir 108 and the wicking surface 306. About 100% of the surface area of the wicking surface 306 is contacted by the volatile material 106. In the operating condition shown in FIG. 25C, the volatile material 106 is diffused through the wicking surface 306 in a complete boost state, whereby the entire wicking surface 306 is in contact with the volatile material 106. In one embodiment, the diffusion rate of the volatile material 106 in FIG. 25C is the greatest during the boost state as compared to the other operating states. In another embodiment, the diffusion rate of the volatile material 106 in FIG. 25C is substantially similar to the diffusion rate of the volatile material 106 in FIG. 25B.

Although three distinct operational states are discussed hereinabove, it should be apparent that numerous operating conditions may exist between the passive state and the boost state. In use, the user typically places the volatile material dispensing system disclosed herein in the passive state. When a user desires a fragrance boost, the user simply rotates the reservoir 108 using the apparatuses described herein to one of any number of boost states. In one embodiment, when the user removes force from the housing 102, the reservoir 108 returns immediately to the passive state position, but the reservoir 108 continues to provide a boost due to the wetting properties of the wicking surface 306. In a different embodiment, a user may lock the reservoir 108 into any other operating condition. For example, the user may position the reservoir 108 in the orientation depicted in FIG. 25A for a time period $t_1$ (see FIG. 26). The user may then rotate the reservoir 108 to the boost state shown in FIG. 25C for a time period $t_2$ when a larger fragrance diffusion rate is desired. Finally, the user may return the reservoir 108 to the passive state depicted in FIG. 25A at a time $t_3$. After a partial or full boost, the wetted wicking surface 306 continues to provide a temporary boost function for a time period $t_4$ until the wicking surface 306 becomes substantially dry and the volatile material 106 is returned to the passive diffusion rate at a time $t_5$. The slope of curve C varies according to the type of material used for the wicking surface, the type of volatile material used, the temperature of the room, the air flow over and around the device, and the surface area of the wicking surface that is contacted by the volatile material.

Although various components are described in a specific shape, such as, for example, circular, rectangular, oval, and the like, it is envisioned that any volatile material dispensing system and the components associated therewith may comprise any shape as is known in the art.

In an alternative embodiment, the reservoirs disclosed herein may be similar or identical to those described in U.S. Pat. No. 7,213,770 and U.S. Pat. No. 7,665,238. Further, the volatile material disclosed in the embodiments herein may be a fragrance or insecticide disposed within a carrier liquid, a deodorizing liquid, or the like. For example, the volatile material may comprise OUST®, an air and carpet sanitizer for household, commercial, and institutional use, or GLADE®, a household deodorant, both sold by S. C. Johnson and Son, Inc., of Racine, Wis. The volatile material may also comprise other actives, such as sanitizers, air fresheners, odor eliminators, mold or mildew inhibitors, insect repellents, and the like, or that have aromatherapeutic properties. The volatile material alternatively comprises any volatile material known to those skilled in the art.

Any of the embodiments described herein may be modified to include any of the structures or methodologies disclosed in connection with different embodiments. Further, the present disclosure is not limited to housing shapes/sizes of the type specifically shown. Still further, the housing of any of the embodiments disclosed herein may be modified to work with any type of volatile material refill unit using the disclosure herein.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A volatile material dispensing system, comprising:
   a housing having at least one opening in a sidewall thereof;
   at least one engagement member extending from the housing;
   a base adapted to interact with the housing, wherein the base includes a mechanical assembly; and
   a reservoir that contains a volatile material and includes a film extending over an open end of the reservoir and having a wicking surface for diffusion of the volatile material, wherein the reservoir rotates from a first upright position in which the volatile material is not in contact with the wicking surface, to a second position in which the volatile material is at least partially in contact with the wicking surface when the at least one engagement member contacts the mechanical assembly.

2. The volatile material dispensing system of claim 1, wherein the at least one engagement member is integral with and extends from an interior portion of the housing.

3. The volatile material dispensing system of claim 1, wherein the housing slideably moves in a downward vertical direction when external force is applied thereto.

4. The volatile material dispensing system of claim 3, wherein the housing moves in an upward vertical direction when external force is removed therefrom.

5. The volatile material dispensing system of claim 1, wherein the housing includes a limited range of upward and downward vertical movement due to interaction between resilient snaps provided on the housing and flexible prongs provided on the base.

6. The volatile material dispensing system of claim 1, wherein the mechanical assembly includes at least one of a support wall, a spring, and a cover member.

7. The volatile material dispensing system of claim 1, wherein the mechanical assembly includes a support wall having a slot provided therein to facilitate rotational movement of the reservoir.

8. A reservoir for a volatile material dispensing system, comprising:
   a base having a sidewall extending therefrom;
   a film having a wicking surface extending over the sidewall to enclose a volatile material within the base and the sidewall; and
   a pair of extension members disposed on opposing sides of at least one of the base and the sidewall,
   wherein the reservoir is designed to mechanically rotate from a first position into a second position about the extension members in response to an external force applied to the reservoir, and
   wherein the base, the sidewall, and the film form a refillable cartridge that is designed to be placed in an operational state within a housing of the volatile material dispensing system and removed for replacement.

9. The reservoir of claim 8, wherein the extension members are provided on ends of the base.

10. The reservoir of claim 8, wherein the extension members are cylindrical posts.

11. The reservoir of claim 8, wherein the film is sealed to a peripheral portion of a blister holding the volatile material, and wherein the blister is held within the base and the sidewall.

12. The reservoir of claim 11, wherein the blister is removable from the base and the sidewall.

13. A reservoir that is designed to be placed in an operational state within a housing of a volatile material dispensing system and removed for replacement, comprising:
   a base having a sidewall extending therefrom;
   a wicking surface extending over the sidewall to enclose a volatile material within the base and the sidewall; and
   at least one extension member extending from the reservoir,
   wherein the reservoir rotates about an axis formed by the extension member between a first operational state in which the volatile material is not in contact with the wicking surface, and a second operational state in which the volatile material is at least partially in contact with the wicking surface.

14. The reservoir of claim 13, wherein the wicking surface comprises a polymer provided in the form of a film.

15. The reservoir of 14, wherein the film has a porosity between about 40% to about 75%.

16. The reservoir of claim 14, wherein the film has a residual oil content of between about 1% to about 16%.

17. The reservoir of claim 13, wherein the wicking surface includes a textured surface on at least one side thereof.

\* \* \* \* \*